US009650438B2

(12) United States Patent
Campbell et al.

(10) Patent No.: US 9,650,438 B2
(45) Date of Patent: May 16, 2017

(54) NUCLEIC ACID ENCODING ANTI-IL13 HUMAN ANTIBODIES

(71) Applicants: Emma Michelle Campbell, Horsham (GB); Sofia Parveen, Horsham (GB); Joe Buechler, Carlsbad, CA (US); Gunars Valkirs, Escondido, CA (US)

(72) Inventors: Emma Michelle Campbell, Horsham (GB); Sofia Parveen, Horsham (GB); Joe Buechler, Carlsbad, CA (US); Gunars Valkirs, Escondido, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/629,587

(22) Filed: Feb. 24, 2015

(65) Prior Publication Data

US 2015/0259411 A1 Sep. 17, 2015
US 2017/0101467 A9 Apr. 13, 2017

Related U.S. Application Data

(60) Continuation of application No. 14/044,314, filed on Oct. 2, 2013, now Pat. No. 8,992,916, which is a division of application No. 12/975,667, filed on Dec. 22, 2010, now Pat. No. 8,580,260, which is a division of application No. 12/091,020, filed as application No. PCT/EP2006/010098 on Oct. 19, 2006, now Pat. No. 7,910,708.

(30) Foreign Application Priority Data

Oct. 21, 2005 (GB) .................................. 0521509.0
Aug. 22, 2006 (GB) .................................. 0616666.4

(51) Int. Cl.
| | |
|---|---|
| *C12N 15/64* | (2006.01) |
| *C07K 16/24* | (2006.01) |
| *C12P 21/02* | (2006.01) |
| *A61K 38/01* | (2006.01) |
| *C12N 15/81* | (2006.01) |
| *A61K 38/12* | (2006.01) |
| *A61K 39/00* | (2006.01) |

(52) U.S. Cl.
CPC .......... *C07K 16/244* (2013.01); *A61K 38/012* (2013.01); *C12N 15/81* (2013.01); *C12P 21/02* (2013.01); *A61K 2039/505* (2013.01); *A61K 2039/507* (2013.01); *C07K 2317/21* (2013.01); *C07K 2317/76* (2013.01); *C07K 2317/92* (2013.01); *Y10S 514/853* (2013.01)

(58) Field of Classification Search
None
See application file for complete search history.

(56) References Cited

U.S. PATENT DOCUMENTS

| 6,468,528 | B1 | 10/2002 | Mak et al. |
|---|---|---|---|
| 6,794,132 | B2 | 9/2004 | Buechler et al. |
| 7,282,206 | B2 | 10/2007 | Wynn et al. |
| 2003/0143199 | A1 | 7/2003 | Carson et al. |
| 2004/0023337 | A1 | 2/2004 | Heavner et al. |
| 2004/0028650 | A1 | 2/2004 | Van Snick et al. |
| 2004/0242841 | A1 | 12/2004 | Cammack et al. |
| 2004/0248260 | A1 | 12/2004 | Heavner et al. |
| 2005/0054055 | A1 | 3/2005 | Kucherlapati et al. |
| 2005/0065327 | A1 | 3/2005 | Monk et al. |
| 2005/0096268 | A1 | 5/2005 | Wynn et al. |
| 2006/0063228 | A1 | 3/2006 | Kasaian et al. |
| 2006/0073148 | A1 | 4/2006 | Tchistiakova et al. |
| 2014/0050735 | A1* | 2/2014 | Ruehl ................. C07K 16/244 424/139.1 |

FOREIGN PATENT DOCUMENTS

| GB | 2403952 | A | 1/2005 |
|---|---|---|---|
| WO | 94/04680 | A1 | 3/1994 |
| WO | 00/36103 | A1 | 6/2000 |
| WO | 00/56771 | A1 | 9/2000 |
| WO | 01/62933 | A2 | 8/2001 |
| WO | 03/007685 | A2 | 1/2003 |
| WO | 03/034984 | A2 | 5/2003 |
| WO | 03/086451 | A1 | 10/2003 |
| WO | 03/092610 | A2 | 11/2003 |
| WO | 03/102157 | A1 | 12/2003 |
| WO | 2004/050850 | A2 | 6/2004 |
| WO | 2005/007699 | A2 | 1/2005 |
| WO | 2005/062967 | A2 | 7/2005 |
| WO | 2005/091853 | A2 | 10/2005 |
| WO | 2005/121177 | A2 | 12/2005 |
| WO | 2005/123126 | A2 | 12/2005 |
| WO | 2006/003407 | A2 | 1/2006 |

(Continued)

OTHER PUBLICATIONS

Akdis et al., Skin-homing, CLA+ memory T cells are activated in atopic dermatitis and regulate IgE by an IL-13—dominated cytokine pattern: IgG4 counter-regulation by CLA—memory T cells. J Immunol. Nov. 1, 1997;159(9):4611-9.
Blanchard et al., Inhibition of human interleukin-13-induced respiratory and oesophageal inflammation by anti-human-interleukin-13 antibody (CAT-354). Clin Exp Allergy. Aug. 2005;35(8):1096-103.
Bree et al., IL-13 blockade reduces lung inflammation after Ascaris suum challenge in cynomolgus monkeys. J Allergy Clin Immunol. May 2007;119(5):1251-7.
Casset et al., A peptide mimetic of an anti-CD4 monoclonal antibody by rational design. Biochemical and Biophysical Research Communications. 307:198-205 (2003).
Communication pursuant to Rule 114(2) EFC (EP Application No. 12173018.8) Oct. 27, 2014.
Communication Pursuant to Rule 114(2) EPC (third party observation in EP06806402) Feb. 16, 2012.
Communication Pursuant to Rule 114(2) EPC (third party observation in EP06806402.1) Jul. 27, 2012.
Communication Pursuant to Rule 114(2) EPC (third party observation in EP06806402.1) Aug. 13, 2013.

(Continued)

*Primary Examiner* — Bridget E Bunner
*Assistant Examiner* — Fozia Hamud

(57) ABSTRACT

The present invention relates to human anti-IL-13 binding molecules, particularly antibodies, and to methods for using anti-IL-13 antibody molecules in diagnosis or treatment of IL-13 related disorders, such as asthma, atopic dermatitis, allergic rhinitis, fibrosis, inflammatory bowel disease and Hodgkin's lymphoma.

20 Claims, No Drawings

(56) References Cited

FOREIGN PATENT DOCUMENTS

| WO | 2006/055638 A2 | | 5/2006 |
|---|---|---|---|
| WO | 2006/085938 A2 | | 8/2006 |
| WO | 2006/124451 A2 | | 11/2006 |
| WO | 2007/036745 A2 | | 4/2007 |
| WO | 2007/041219 A2 | | 4/2007 |
| WO | WO 2007/045477 | * | 4/2007 |
| WO | 2007/076062 A2 | | 7/2007 |
| WO | 2007/080174 A2 | | 7/2007 |
| WO | 2007/085815 A2 | | 8/2007 |

OTHER PUBLICATIONS

Eum et al., IL-13 may mediate allergen-induced hyperresponsiveness independently of IL-5 or eotaxin by effects on airway smooth muscle. Am J Physiol Lung Cell Mol Physiol. Mar. 2005;288(3):L576-84.

Gauvreau et al., The effects of IMA-638 on allergen induced airway responses in subjects with mild atopic asthma. European Respiratory Journal. 2008;32(52):827.

Hamid et al., In vivo expression of IL-12 and IL-13 in atopic dermatitis. J Allergy Clin Immunol. Jul. 1996;98(1):225-31.

Katagiri et al., Increased levels of IL-13 mRNA, but not IL-4 mRNA, are found in vivo in peripheral blood mononuclear cells (PBMC) of patients with atopic dermatitis (AD). Clin Exp Immunol. May 1997;108(2):289-94.

Kim et al., Topical delivery of interleukin-13 antisense oligonucleotides with cationic elastic liposome for the treatment of atopic dermatitis. J Gene Med. Jan. 2009;11(1):26-37.

Kumar et al., Effects of anticytokine therapy in a mouse model of chronic asthma. Am J Respir Crit Care Med. Nov. 15, 2004;170(10):1043-8.

Lee et al., Transgenic mice which overproduce Th2 cytokines develop spontaneous atopic dermatitis and asthma. Int Immunol. Aug. 2004;16(8):1155-60. Transgenic mice which overproduce Th2 cytokines develop spontaneous atopic dermatitis and asthma. Int Immunol. Aug. 2004;16(8):1155-60.

Madhankumar et al., Alanine-scanning mutagenesis of alpha-helix D segment of interleukin-13 reveals new functionally important residues of the cytokine. J Biol Chem. Nov. 8, 2002;277(45):43194-205.

Madhankumar et al., Interleukin 13 mutants of enhanced avidity toward the glioma-associated receptor, IL13Ralpha2. Neoplasia. Jan.-Feb. 2004;6(1):15-22.

Pease et al., Eotaxin and asthma. Curr Opin Pharmacol. Jun. 2001;1(3):248-53.

Rudikoff et al., Single amino acid substitution altering antigen-binding specificity. Proc. Natl. Avad. Sci. USA 79:1979-1983 (Mar. 1982).

Ruth et al., Interleukin 4 and 13 Participation in Mycobacterial (type-1) and schistosomal (type-2) Antigen-Elicited Pulmonary Granuloma Formation: Multiparameter Analysis of Cellular Recruitment, Chemokine Expression and Cytokine Networks. Cytokine 12(5):432-444 (May 2000).

Stedman's Online Dictionary, downloaded on Feb. 20, 2014, 3 pages.

Tamura et al., Structural Correlates of an Anticarcinoma Antibody: Identification of Specificity-Determining Residues (SDRs) and Development of a Minimally Immunogenic Antibody Variant by Retention of SDRs Only. J Immunol 164:1432-1441 (2000).

Yang et al., Anti-IL-13 monoclonal antibody inhibits airway hyperresponsiveness, inflammation and airway remodeling. Cytokine. Dec. 21, 2004;28(6):224-32.

Yang et al., Therapeutic dosing with anti-interleukin-13 monoclonal antibody inhibits asthma progression in mice. J Pharmacology Exper Therapeutics. 2005;313(1):8-15.

Zheng et al., Transgenic expression of interleukin-13 in the skin induces a pruritic dermatitis and skin remodeling. J Invest Dermatol. Mar. 2009;129(3):742-51.

* cited by examiner

SEQUENCE LISTING

<160> NUMBER OF SEQ IDS NOS: 42

<210> SEQ ID NO 1
<211> LENGTH: 8
<212> TYPE: PRT

<213> ORGANISM: Homo sapiens

<400> SEQUENCE: 1

Gly Phe Thr Phe Ser Asn Tyr Gly
1               5

<210> SEQ ID NO 2
<211> LENGTH: 8
<212> TYPE: PRT
<213> ORGANISM: Homo sapiens

<400> SEQUENCE: 2

Gly Phe Thr Phe Ser Ser Tyr Gly
1               5

<210> SEQ ID NO 3
<211> LENGTH: 7
<212> TYPE: PRT
<213> ORGANISM: Homo sapiens

<400> SEQUENCE: 3

Ile Trp Tyr Asp Gly Ser Asn
1               5

<210> SEQ ID NO 4
<211> LENGTH: 8
<212> TYPE: PRT
<213> ORGANISM: Homo sapiens

<400> SEQUENCE: 4

Val Lys Gly Ser Gly Asp Ile Pro
1               5

<210> SEQ ID NO 5
<211> LENGTH: 9
<212> TYPE: PRT
<213> ORGANISM: Homo sapiens

<400> SEQUENCE: 5

Ala Arg Leu Trp Phe Gly Asp Leu Asp
1               5

<210> SEQ ID NO 6
<211> LENGTH: 5
<212> TYPE: PRT
<213> ORGANISM: Homo sapiens

<400> SEQUENCE: 6

Asn Tyr Gly Met His
1               5

<210> SEQ ID NO 7
<211> LENGTH: 5
<212> TYPE: PRT
<213> ORGANISM: Homo sapiens

<400> SEQUENCE: 7

Ser Tyr Gly Met His
1               5

<210> SEQ ID NO 8
<211> LENGTH: 17
<212> TYPE: PRT
<213> ORGANISM: Homo sapiens

```
<400> SEQUENCE: 8

Ile Ile Trp Tyr Asp Gly Ser Asn Lys Tyr Tyr Ala Asp Ser Val Lys
1               5                   10                  15
Gly

<210> SEQ ID NO 9
<211> LENGTH: 9
<212> TYPE: PRT
<213> ORGANISM: Homo sapiens

<400> SEQUENCE: 9

Gly Ser Gly Asp Ile Pro Phe Asp Tyr
1               5

<210> SEQ ID NO 10
<211> LENGTH: 11
<212> TYPE: PRT
<213> ORGANISM: Homo sapiens

<400> SEQUENCE: 10

Leu Trp Phe Gly Asp Leu Asp Ala Phe Asp Ile
1               5                   10

<210> SEQ ID NO 11
<211> LENGTH: 6
<212> TYPE: PRT
<213> ORGANISM: Homo sapiens

<400> SEQUENCE: 11

Gln Ser Val Ser Ser Tyr
1               5

<210> SEQ ID NO 12
<211> LENGTH: 2
<212> TYPE: PRT
<213> ORGANISM: Homo sapiens

<400> SEQUENCE: 12

Asp Ala
1

<210> SEQ ID NO 13
<211> LENGTH: 9
<212> TYPE: PRT
<213> ORGANISM: Homo sapiens

<400> SEQUENCE: 13

His Gln Arg Ser His Trp Pro Pro Ile
1               5

<210> SEQ ID NO 14
<211> LENGTH: 9
<212> TYPE: PRT
<213> ORGANISM: Homo sapiens

<400> SEQUENCE: 14

Gln Gln Arg Ser Ser Trp Pro Pro Val
1               5

<210> SEQ ID NO 15
<211> LENGTH: 9
<212> TYPE: PRT
<213> ORGANISM: Homo sapiens
```

<400> SEQUENCE: 15

His Gln Arg Ser Ser Trp Pro Pro Ile
1               5

<210> SEQ ID NO 16
<211> LENGTH: 11
<212> TYPE: PRT
<213> ORGANISM: Homo sapiens

<400> SEQUENCE: 16

Arg Ala Ser Gln Ser Val Ser Ser Tyr Leu Ala
1               5                   10

<210> SEQ ID NO 17
<211> LENGTH: 11
<212> TYPE: PRT
<213> ORGANISM: Homo sapiens

<400> SEQUENCE: 17

Arg Ala Gly Gln Ser Val Ser Ser Tyr Leu Val
1               5                   10

<210> SEQ ID NO 18

<400> SEQUENCE: 18

000

<210> SEQ ID NO 19
<211> LENGTH: 7
<212> TYPE: PRT
<213> ORGANISM: Homo sapiens

<400> SEQUENCE: 19

Asp Ala Ser Asn Arg Ala Thr
1               5

<210> SEQ ID NO 20
<211> LENGTH: 11
<212> TYPE: PRT
<213> ORGANISM: Homo sapiens

<400> SEQUENCE: 20

His Gln Arg Ser His Trp Pro Pro Ile Phe Thr
1               5                   10

<210> SEQ ID NO 21
<211> LENGTH: 11
<212> TYPE: PRT
<213> ORGANISM: Homo sapiens

<400> SEQUENCE: 21

Gln Gln Arg Ser Ser Trp Pro Pro Val Tyr Thr
1               5                   10

<210> SEQ ID NO 22
<211> LENGTH: 11
<212> TYPE: PRT
<213> ORGANISM: Homo sapiens

<400> SEQUENCE: 22

His Gln Arg Ser Ser Trp Pro Pro Ile Phe Thr
1               5                   10

-continued

```
<210> SEQ ID NO 23
<211> LENGTH: 115
<212> TYPE: PRT
<213> ORGANISM: Homo sapiens

<400> SEQUENCE: 23

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Gly Ser Gly Asp Ile Pro Phe Asp Tyr Trp Gly Gln Gly Thr
            100                 105                 110

Leu Val Thr
        115

<210> SEQ ID NO 24
<211> LENGTH: 345
<212> TYPE: DNA
<213> ORGANISM: Homo sapiens
<220> FEATURE:
<221> NAME/KEY: CDS
<222> LOCATION: (1)..(345)

<400> SEQUENCE: 24 gaa gtg cag ctg gtg gag tct ggg gga ggc gtg gtc cag cct ggg agg      48
Glu Val Gln Leu Val Glu Ser Gly Gly Gly Val Val Gln Pro Gly Arg
1               5                   10                  15 tcc ctg aga ctc tcc tgt gca gcg tct gga ttc acc ttc agt aac tat      96
Ser Leu Arg Leu Ser Cys Ala Ala Ser Gly Phe Thr Phe Ser Asn Tyr
            20                  25                  30 ggc atg cac tgg gtc cgc cag gct cca ggc aag ggg ctg gag tgg gtg     144
Gly Met His Trp Val Arg Gln Ala Pro Gly Lys Gly Leu Glu Trp Val
        35                  40                  45 gca att ata tgg tat gat gga agt aat aaa tac tat gca gac tcc gtg     192
Ala Ile Ile Trp Tyr Asp Gly Ser Asn Lys Tyr Tyr Ala Asp Ser Val
    50                  55                  60 aag ggc cga ttc acc atc tcc aga gac aat tcc aag aac acg ctg tat     240
Lys Gly Arg Phe Thr Ile Ser Arg Asp Asn Ser Lys Asn Thr Leu Tyr
65                  70                  75                  80 ctg caa atg aac agt ctg aga gcc gag gac acg gct gtg tat tac tgt     288
Leu Gln Met Asn Ser Leu Arg Ala Glu Asp Thr Ala Val Tyr Tyr Cys
                85                  90                  95 gtg aaa gga tct ggg gat att ccc ttt gac tac tgg ggc cag gga acc     336
Val Lys Gly Ser Gly Asp Ile Pro Phe Asp Tyr Trp Gly Gln Gly Thr
            100                 105                 110 ctg gtc acc                                                         345
Leu Val Thr
        115

<210> SEQ ID NO 25
<211> LENGTH: 104
<212> TYPE: PRT
<213> ORGANISM: Homo sapiens
```

<400> SEQUENCE: 25

Glu Ile Val Leu Thr Gln Ser Pro Ala Thr Leu Ser Ser Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys His Gln Arg Ser His Trp Pro Pro
                85                  90                  95

Ile Phe Thr Phe Gly Pro Gly Thr
            100

<210> SEQ ID NO 26
<211> LENGTH: 312
<212> TYPE: DNA
<213> ORGANISM: Homo sapiens
<220> FEATURE:
<221> NAME/KEY: CDS
<222> LOCATION: (1)..(312)

<400> SEQUENCE: 26 gaa att gtg ttg acg cag tct cca gcc acc ctg tct tcg tct cca ggg     48
Glu Ile Val Leu Thr Gln Ser Pro Ala Thr Leu Ser Ser Ser Pro Gly
1               5                   10                  15 gaa aga gcc acc ctc tcc tgc agg gcc agt cag agt gtt agc agc tac     96
Glu Arg Ala Thr Leu Ser Cys Arg Ala Ser Gln Ser Val Ser Ser Tyr
            20                  25                  30 tta gcc tgg tac caa cag aaa cct ggc cag gct ccc agg ctc ctc atc    144
Leu Ala Trp Tyr Gln Gln Lys Pro Gly Gln Ala Pro Arg Leu Leu Ile
        35                  40                  45 tat gat gca tcc aac agg gcc act ggc atc cca gcc agg ttc agt ggc    192
Tyr Asp Ala Ser Asn Arg Ala Thr Gly Ile Pro Ala Arg Phe Ser Gly
    50                  55                  60 agt ggg tct ggg aca gac ttc act ctc acc atc agc agc cta gag cct    240
Ser Gly Ser Gly Thr Asp Phe Thr Leu Thr Ile Ser Ser Leu Glu Pro
65                  70                  75                  80 gaa gat ttt gca gtc tat tac tgt cat cag cgt agc cac tgg cct ccc    288
Glu Asp Phe Ala Val Tyr Tyr Cys His Gln Arg Ser His Trp Pro Pro
                85                  90                  95 ata ttc act ttc ggc cct ggg acc                                    312
Ile Phe Thr Phe Gly Pro Gly Thr
            100

<210> SEQ ID NO 27
<211> LENGTH: 115
<212> TYPE: PRT
<213> ORGANISM: Homo sapiens

<400> SEQUENCE: 27

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

```
Ala Ile Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Val Lys Gly Ser Gly Asp Ile Pro Phe Asp Tyr Trp Gly Gln Gly Thr
            100                 105                 110

Leu Val Thr
        115

<210> SEQ ID NO 28
<211> LENGTH: 345
<212> TYPE: DNA
<213> ORGANISM: Homo sapiens
<220> FEATURE:
<221> NAME/KEY: CDS
<222> LOCATION: (1)..(345)

<400> SEQUENCE: 28 gaa gtg cag ctg gtg gag tct ggg gga ggc gtg gtc cag cct ggg agg      48
Glu Val Gln Leu Val Glu Ser Gly Gly Gly Val Val Gln Pro Gly Arg
  1               5                  10                  15 tcc ctg aga ctc tcc tgt gca gcg tct gga ttc acc ttc agt aac tat      96
Ser Leu Arg Leu Ser Cys Ala Ala Ser Gly Phe Thr Phe Ser Asn Tyr
                 20                  25                  30 ggc atg cac tgg gtc cgc cag gct cca ggc aag ggg ctg gag tgg gtg     144
Gly Met His Trp Val Arg Gln Ala Pro Gly Lys Gly Leu Glu Trp Val
             35                  40                  45 gca att ata tgg tat gat gga agt aat aaa tac tat gca gac tcc gtg     192
Ala Ile Ile Trp Tyr Asp Gly Ser Asn Lys Tyr Tyr Ala Asp Ser Val
     50                  55                  60 aag ggc cga ttc acc atc tcc aga gac aat tcc aag aac acg ctg tat     240
Lys Gly Arg Phe Thr Ile Ser Arg Asp Asn Ser Lys Asn Thr Leu Tyr
 65                  70                  75                  80 ctg caa atg aac agt ctg aga gcc gag gac acg gct gtg tat tac tgt     288
Leu Gln Met Asn Ser Leu Arg Ala Glu Asp Thr Ala Val Tyr Tyr Cys
                 85                  90                  95 gtg aaa gga tct ggg gat att ccc ttt gac tac tgg ggc cag gga acc     336
Val Lys Gly Ser Gly Asp Ile Pro Phe Asp Tyr Trp Gly Gln Gly Thr
            100                 105                 110 ctg gtc acc                                                         345
Leu Val Thr
        115

<210> SEQ ID NO 29
<211> LENGTH: 104
<212> TYPE: PRT
<213> ORGANISM: Homo sapiens

<400> SEQUENCE: 29

Glu Ile Val Leu Thr Gln Ser Pro Ala Thr Leu Ser Ser Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Thr Pro Ala Arg Phe Ser Gly
     50                  55                  60
```

```
Ser Gly Ser Gly Thr Asp Phe Thr Leu Thr Ile Ser Ser Leu Glu Pro
 65                  70                  75                  80

Glu Asp Phe Ala Val Tyr Tyr Cys His Gln Arg Ser His Trp Pro Pro
                 85                  90                  95

Ile Phe Thr Phe Gly Pro Gly Thr
                100
```

<210> SEQ ID NO 30
<211> LENGTH: 312
<212> TYPE: DNA
<213> ORGANISM: Homo sapiens
<220> FEATURE:
<221> NAME/KEY: CDS
<222> LOCATION: (1)..(312)

<400> SEQUENCE: 30

```
gaa att gtg ttg acg cag tcc cca gcc acc ctg tct tcg tct cca ggg      48
Glu Ile Val Leu Thr Gln Ser Pro Ala Thr Leu Ser Ser Ser Pro Gly
  1               5                  10                  15 gaa aga gcc acc ctc tcc tgc agg gcc agt cag agt gtt agc agc tac      96
Glu Arg Ala Thr Leu Ser Cys Arg Ala Ser Gln Ser Val Ser Ser Tyr
             20                  25                  30 tta gcc tgg tac caa cag aaa cct ggc cag gct ccc agg ctc ctc atc    144
Leu Ala Trp Tyr Gln Gln Lys Pro Gly Gln Ala Pro Arg Leu Leu Ile
         35                  40                  45 tat gat gca tcc aac agg gcc act ggc acc cca gcc agg ttc agt ggc    192
Tyr Asp Ala Ser Asn Arg Ala Thr Gly Thr Pro Ala Arg Phe Ser Gly
     50                  55                  60 agt ggg tct ggg aca gac ttc act ctc acc atc agc agc cta gag cct    240
Ser Gly Ser Gly Thr Asp Phe Thr Leu Thr Ile Ser Ser Leu Glu Pro
 65                  70                  75                  80 gaa gat ttt gca gtc tat tac tgt cat cag cgt agc cac tgg cct ccc    288
Glu Asp Phe Ala Val Tyr Tyr Cys His Gln Arg Ser His Trp Pro Pro
                 85                  90                  95 ata ttc act ttc ggc cct ggg acc                                    312
Ile Phe Thr Phe Gly Pro Gly Thr
                100
```

<210> SEQ ID NO 31
<211> LENGTH: 117
<212> TYPE: PRT
<213> ORGANISM: Homo sapiens

<400> SEQUENCE: 31

```
Glu Val Gln Leu Val Glu Ser Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Ile Ile Trp Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Leu Trp Phe Gly Asp Leu Asp Ala Phe Asp Ile Trp Gly Gln
                100                 105                 110

Gly Thr Met Val Thr
                115
```

<210> SEQ ID NO 32
<211> LENGTH: 351
<212> TYPE: DNA
<213> ORGANISM: Homo sapiens
<220> FEATURE:
<221> NAME/KEY: CDS
<222> LOCATION: (1)..(351)

<400> SEQUENCE: 32

| | | | | | | | | | | | | | | | | |
|---|---|---|---|---|---|---|---|---|---|---|---|---|---|---|---|---|
| gaa | gtg | cag | ctg | gtg | gag | tct | ggg | gga | ggc | gtg | gtc | cag | cct | ggg | agg | 48 |
| Glu | Val | Gln | Leu | Val | Glu | Ser | Gly | Gly | Gly | Val | Val | Gln | Pro | Gly | Arg | |
| 1 | | | | 5 | | | | | 10 | | | | | 15 | | |
| tcc | ctg | aga | ctc | tcc | tgt | gca | gcg | tct | gga | ttc | acc | ttc | agt | agc | tat | 96 |
| Ser | Leu | Arg | Leu | Ser | Cys | Ala | Ala | Ser | Gly | Phe | Thr | Phe | Ser | Ser | Tyr | |
| | | | 20 | | | | | 25 | | | | | 30 | | | |
| ggc | atg | cac | tgg | gtc | cgc | cag | gct | cca | ggc | aag | ggg | ctg | gag | tgg | gtg | 144 |
| Gly | Met | His | Trp | Val | Arg | Gln | Ala | Pro | Gly | Lys | Gly | Leu | Glu | Trp | Val | |
| | | 35 | | | | | 40 | | | | | 45 | | | | |
| gca | att | ata | tgg | tat | gat | gga | agt | aat | aaa | tac | tat | gcg | gac | tcc | gtg | 192 |
| Ala | Ile | Ile | Trp | Tyr | Asp | Gly | Ser | Asn | Lys | Tyr | Tyr | Ala | Asp | Ser | Val | |
| 50 | | | | | 55 | | | | | 60 | | | | | | |
| aag | ggc | cga | ttc | acc | atc | tcc | aga | gac | aat | tcc | aag | aac | acg | ctg | tat | 240 |
| Lys | Gly | Arg | Phe | Thr | Ile | Ser | Arg | Asp | Asn | Ser | Lys | Asn | Thr | Leu | Tyr | |
| 65 | | | | 70 | | | | | 75 | | | | | 80 | | |
| ctg | caa | atg | aac | agc | ctg | aga | gcc | gag | gac | acg | gct | gtg | tat | tac | tgt | 288 |
| Leu | Gln | Met | Asn | Ser | Leu | Arg | Ala | Glu | Asp | Thr | Ala | Val | Tyr | Tyr | Cys | |
| | | | 85 | | | | | 90 | | | | | 95 | | | |
| gcg | agg | cta | tgg | ttc | ggg | gac | tta | gat | gct | ttt | gat | atc | tgg | ggc | caa | 336 |
| Ala | Arg | Leu | Trp | Phe | Gly | Asp | Leu | Asp | Ala | Phe | Asp | Ile | Trp | Gly | Gln | |
| | | 100 | | | | | 105 | | | | | 110 | | | | |
| ggg | aca | atg | gtc | acc | | | | | | | | | | | | 351 |
| Gly | Thr | Met | Val | Thr | | | | | | | | | | | | |
| | | 115 | | | | | | | | | | | | | | |

<210> SEQ ID NO 33
<211> LENGTH: 104
<212> TYPE: PRT
<213> ORGANISM: Homo sapiens

<400> SEQUENCE: 33

Glu Ile Val Leu Thr Gln Ser Pro Ala Thr Leu Ser Leu Ser Pro Gly
1               5                   10                  15

Glu Arg Ala Ile Leu Ser Cys Arg Ala Gly Gln Ser Val Ser Ser Tyr
            20                  25                  30

Leu Val Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Ser Trp Pro Pro
                85                  90                  95

Val Tyr Thr Phe Gly Gln Gly Thr
            100

<210> SEQ ID NO 34
<211> LENGTH: 312
<212> TYPE: DNA
<213> ORGANISM: Homo sapiens
<220> FEATURE:
<221> NAME/KEY: CDS

<222> LOCATION: (1)..(312)

<400> SEQUENCE: 34

```
gaa att gtg ttg acg cag tct cca gcc acc ctg tct ttg tct cca ggg      48
Glu Ile Val Leu Thr Gln Ser Pro Ala Thr Leu Ser Leu Ser Pro Gly
1               5                   10                  15 gaa aga gcc atc ctc tcc tgc agg gcc ggt cag agt gtt agc agt tac      96
Glu Arg Ala Ile Leu Ser Cys Arg Ala Gly Gln Ser Val Ser Ser Tyr
            20                  25                  30 tta gtc tgg tac caa cag aaa cct ggc cag gct ccc agg ctc ctc atc     144
Leu Val Trp Tyr Gln Gln Lys Pro Gly Gln Ala Pro Arg Leu Leu Ile
        35                  40                  45 tat gat gca tcc aac agg gcc act ggc atc cca gcc agg ttc agt ggc     192
Tyr Asp Ala Ser Asn Arg Ala Thr Gly Ile Pro Ala Arg Phe Ser Gly
    50                  55                  60 agt ggg tct ggg aca gac ttc act ctc acc atc agc agc cta gag cct     240
Ser Gly Ser Gly Thr Asp Phe Thr Leu Thr Ile Ser Ser Leu Glu Pro
65                  70                  75                  80 gaa gat ttt gca gtt tat tac tgt cag cag cgc agc agc tgg cct ccg     288
Glu Asp Phe Ala Val Tyr Tyr Cys Gln Gln Arg Ser Ser Trp Pro Pro
                85                  90                  95 gtg tac act ttt ggc cag ggg acc                                     312
Val Tyr Thr Phe Gly Gln Gly Thr
                100
```

<210> SEQ ID NO 35
<211> LENGTH: 117
<212> TYPE: PRT
<213> ORGANISM: Homo sapiens

<400> SEQUENCE: 35

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Trp Phe Gly Asp Leu Asp Ala Phe Asp Ile Trp Gly Gln
            100                 105                 110

Gly Thr Met Val Thr
        115
```

<210> SEQ ID NO 36
<211> LENGTH: 351
<212> TYPE: DNA
<213> ORGANISM: Homo sapiens
<220> FEATURE:
<221> NAME/KEY: CDS
<222> LOCATION: (1)..(351)

<400> SEQUENCE: 36

```
cag gtg cag ctg gtg cag tct ggg gga ggc gtg gtc cag cct ggg agg      48
Gln Val Gln Leu Val Gln Ser Gly Gly Gly Val Val Gln Pro Gly Arg
1               5                   10                  15
```

```
tcc ctg aga ctc tcc tgt gcg gcg tct gga ttc acc ttc agt agc tat    96
Ser Leu Arg Leu Ser Cys Ala Ala Ser Gly Phe Thr Phe Ser Ser Tyr
        20                  25                  30 ggc atg cac tgg gtc cgc cag gct cca ggc aag ggg ctg gag tgg gtg   144
Gly Met His Trp Val Arg Gln Ala Pro Gly Lys Gly Leu Glu Trp Val
            35                  40                  45 gca att ata tgg tat gat gga agt aat aaa tac tat gcg gac tcc gtg   192
Ala Ile Ile Trp Tyr Asp Gly Ser Asn Lys Tyr Tyr Ala Asp Ser Val
 50                  55                  60 aag ggc cga ttc acc atc tcc aga gac aat tcc aag aac acg cta tat   240
Lys Gly Arg Phe Thr Ile Ser Arg Asp Asn Ser Lys Asn Thr Leu Tyr
 65                  70                  75                  80 cta caa atg aac agc ctg aga gcc gag gac acg gct gtg tat tac tgt   288
Leu Gln Met Asn Ser Leu Arg Ala Glu Asp Thr Ala Val Tyr Tyr Cys
                 85                  90                  95 gcg agg cta tgg ttc ggg gac tta gat gct ttt gat atc tgg ggc caa   336
Ala Arg Leu Trp Phe Gly Asp Leu Asp Ala Phe Asp Ile Trp Gly Gln
            100                 105                 110 ggg aca atg gtc acc                                                351
Gly Thr Met Val Thr
        115

<210> SEQ ID NO 37
<211> LENGTH: 104
<212> TYPE: PRT
<213> ORGANISM: Homo sapiens

<400> SEQUENCE: 37

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys His Gln Arg Ser Ser Trp Pro Pro
                 85                  90                  95

Ile Phe Thr Phe Gly Pro Gly Thr
            100

<210> SEQ ID NO 38
<211> LENGTH: 312
<212> TYPE: DNA
<213> ORGANISM: Homo sapiens
<220> FEATURE:
<221> NAME/KEY: CDS
<222> LOCATION: (1)..(312)

<400> SEQUENCE: 38 gaa att gtg ttg acg cag tct cca gcc acc ctg tct ttg tct cca ggg    48
Glu Ile Val Leu Thr Gln Ser Pro Ala Thr Leu Ser Leu Ser Pro Gly
 1               5                  10                  15 gaa aga gcc acc ctc tcc tgc agg gcc agt cag agt gtt agc agc tac    96
Glu Arg Ala Thr Leu Ser Cys Arg Ala Ser Gln Ser Val Ser Ser Tyr
            20                  25                  30 tta gcc tgg tac caa cag aaa cct ggc cag gct ccc agg ctc ctc atc   144
Leu Ala Trp Tyr Gln Gln Lys Pro Gly Gln Ala Pro Arg Leu Leu Ile
         35                  40                  45
```

| | | | | | | | | | | | | |
|---|---|---|---|---|---|---|---|---|---|---|---|---|
| tat | gat | gca | tcc | aac | agg | gcc | act | ggc | atc | cca | gcc | agg | ttc | agt | ggc | 192 |
| Tyr | Asp | Ala | Ser | Asn | Arg | Ala | Thr | Gly | Ile | Pro | Ala | Arg | Phe | Ser | Gly | |
| | | 50 | | | | 55 | | | | 60 | | | | | | |

| agt | ggg | tct | ggg | aca | gac | ttc | act | ctc | acc | atc | agc | agc | cta | gag | cct | 240 |
| Ser | Gly | Ser | Gly | Thr | Asp | Phe | Thr | Leu | Thr | Ile | Ser | Ser | Leu | Glu | Pro | |
| 65 | | | | | 70 | | | | | 75 | | | | | 80 | |

| gaa | gat | ttt | gcg | gtt | tat | tac | tgt | cat | cag | cgt | agc | agc | tgg | ccc | ccg | 288 |
| Glu | Asp | Phe | Ala | Val | Tyr | Tyr | Cys | His | Gln | Arg | Ser | Ser | Trp | Pro | Pro | |
| | | | | 85 | | | | 90 | | | | 95 | | | | |

| ata | ttc | act | ttc | ggc | cct | ggg | acc | | | | | | | | | 312 |
| Ile | Phe | Thr | Phe | Gly | Pro | Gly | Thr | | | | | | | | | |
| 100 | | | | | | | | | | | | | | | | |

<210> SEQ ID NO 39
<211> LENGTH: 236
<212> TYPE: PRT
<213> ORGANISM: Homo sapiens

<400> SEQUENCE: 39

Met Ser Val Leu Thr Gln Val Leu Ala Leu Leu Leu Trp Leu Thr
1               5                   10                  15

Gly Thr Arg Cys Glu Ile Val Leu Thr Gln Ser Pro Ala Thr Leu Ser
            20                  25                  30

Leu Ser Pro Gly Glu Arg Ala Ile Leu Ser Cys Arg Ala Gly Gln Ser
        35                  40                  45

Val Ser Ser Tyr Leu Val Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Ser Trp Pro Pro Val Tyr Thr Phe Gly Gln Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 40
<211> LENGTH: 711
<212> TYPE: DNA
<213> ORGANISM: Homo sapiens
<220> FEATURE:
<221> NAME/KEY: CDS
<222> LOCATION: (1)..(711)

```
<400> SEQUENCE: 40 atg agt gtg ctc act cag gtc ctg gcg ttg ctg ctg tgg ctt aca      48
Met Ser Val Leu Thr Gln Val Leu Ala Leu Leu Leu Trp Leu Thr
1               5                   10                  15 ggt acg cgt tgt gaa att gtg ttg acg cag tct cca gcc acc ctg tct  96
Gly Thr Arg Cys Glu Ile Val Leu Thr Gln Ser Pro Ala Thr Leu Ser
            20                  25                  30 ttg tct cca ggg gaa aga gcc atc ctc tcc tgc agg gcc ggt cag agt 144
Leu Ser Pro Gly Glu Arg Ala Ile Leu Ser Cys Arg Ala Gly Gln Ser
        35                  40                  45 gtt agc agt tac tta gtc tgg tac caa cag aaa cct ggc cag gct ccc 192
Val Ser Ser Tyr Leu Val Trp Tyr Gln Gln Lys Pro Gly Gln Ala Pro
    50                  55                  60 agg ctc ctc atc tat gat gca tcc aac agg gcc act ggc atc cca gcc 240
Arg Leu Leu Ile Tyr Asp Ala Ser Asn Arg Ala Thr Gly Ile Pro Ala
65                  70                  75                  80 agg ttc agt ggc agt ggg tct ggg aca gac ttc act ctc acc atc agc 288
Arg Phe Ser Gly Ser Gly Ser Gly Thr Asp Phe Thr Leu Thr Ile Ser
                85                  90                  95 agc cta gag cct gaa gat ttt gca gtt tat tac tgt cag cag cgc agc 336
Ser Leu Glu Pro Glu Asp Phe Ala Val Tyr Tyr Cys Gln Gln Arg Ser
            100                 105                 110 agc tgg cct ccg gtg tac act ttt ggc cag ggg acc aag ctt gaa atc 384
Ser Trp Pro Pro Val Tyr Thr Phe Gly Gln Gly Thr Lys Leu Glu Ile
        115                 120                 125 aaa cga act gtg gct gca cca tct gtc ttc atc ttc ccg cca tct gat 432
Lys Arg Thr Val Ala Ala Pro Ser Val Phe Ile Phe Pro Pro Ser Asp
    130                 135                 140 gag cag ttg aaa tct gga act gcc tct gtt gtg tgc ctg ctg aat aac 480
Glu Gln Leu Lys Ser Gly Thr Ala Ser Val Val Cys Leu Leu Asn Asn
145                 150                 155                 160 ttc tat ccc aga gag gcc aaa gta cag tgg aag gtg gat aac gcc ctc 528
Phe Tyr Pro Arg Glu Ala Lys Val Gln Trp Lys Val Asp Asn Ala Leu
                165                 170                 175 caa tcg ggt aac tcc cag gag agt gtc aca gag cag gac agc aag gac 576
Gln Ser Gly Asn Ser Gln Glu Ser Val Thr Glu Gln Asp Ser Lys Asp
            180                 185                 190 agc acc tac agc ctc agc agc acc ctg acg ctg agc aaa gca gac tac 624
Ser Thr Tyr Ser Leu Ser Ser Thr Leu Thr Leu Ser Lys Ala Asp Tyr
        195                 200                 205 gag aaa cac aaa gtc tac gcc tgc gaa gtc acc cat cag ggc ctg agc 672
Glu Lys His Lys Val Tyr Ala Cys Glu Val Thr His Gln Gly Leu Ser
    210                 215                 220 tcg ccc gtc aca aag agc ttc aac agg gga gag tgt tag             711
Ser Pro Val Thr Lys Ser Phe Asn Arg Gly Glu Cys
225                 230                 235

<210> SEQ ID NO 41
<211> LENGTH: 469
<212> TYPE: PRT
<213> ORGANISM: Homo sapiens

<400> SEQUENCE: 41

Met Ala Trp Val Trp Thr Leu Pro Phe Leu Met Ala Ala Ala Gln Ser
1               5                   10                  15

Val Gln Ala Glu Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45
```

```
Ser Ser Tyr Gly Met His Trp Val Arg Gln Ala Pro Gly Lys Gly Leu
    50                  55                  60
Glu Trp Val Ala Ile Ile Trp Tyr Asp Gly Ser Asn Lys Tyr Tyr Ala
65                  70                  75                  80
Asp Ser Val Lys Gly Arg Phe Thr Ile Ser Arg Asp Asn Ser Lys Asn
                85                  90                  95
Thr Leu Tyr Leu Gln Met Asn Ser Leu Arg Ala Glu Asp Thr Ala Val
            100                 105                 110
Tyr Tyr Cys Ala Arg Leu Trp Phe Gly Asp Leu Asp Ala Phe Asp Ile
            115                 120                 125
Trp Gly Gln Gly Thr Met Val Thr Val Ser Ser Ala Ser Thr Lys Gly
        130                 135                 140
Pro Ser Val Phe Pro Leu Ala Pro Ser Ser Lys Ser Thr Ser Gly Gly
145                 150                 155                 160
Thr Ala Ala Leu Gly Cys Leu Val Lys Asp Tyr Phe Pro Glu Pro Val
                165                 170                 175
Thr Val Ser Trp Asn Ser Gly Ala Leu Thr Ser Gly Val His Thr Phe
            180                 185                 190
Pro Ala Val Leu Gln Ser Ser Gly Leu Tyr Ser Leu Ser Ser Val Val
            195                 200                 205
Thr Val Pro Ser Ser Ser Leu Gly Thr Gln Thr Tyr Ile Cys Asn Val
        210                 215                 220
Asn His Lys Pro Ser Asn Thr Lys Val Asp Lys Arg Val Glu Pro Lys
225                 230                 235                 240
Ser Cys Asp Lys Thr His Thr Cys Pro Pro Cys Pro Ala Pro Glu Leu
                245                 250                 255
Leu Gly Gly Pro Ser Val Phe Leu Phe Pro Pro Lys Pro Lys Asp Thr
            260                 265                 270
Leu Met Ile Ser Arg Thr Pro Glu Val Thr Cys Val Val Val Asp Val
            275                 280                 285
Ser His Glu Asp Pro Glu Val Lys Phe Asn Trp Tyr Val Asp Gly Val
        290                 295                 300
Glu Val His Asn Ala Lys Thr Lys Pro Arg Glu Glu Gln Tyr Asn Ser
305                 310                 315                 320
Thr Tyr Arg Val Val Ser Val Leu Thr Val Leu His Gln Asp Trp Leu
                325                 330                 335
Asn Gly Lys Glu Tyr Lys Cys Lys Val Ser Asn Lys Ala Leu Pro Ala
            340                 345                 350
Pro Ile Glu Lys Thr Ile Ser Lys Ala Lys Gly Gln Pro Arg Glu Pro
            355                 360                 365
Gln Val Tyr Thr Leu Pro Pro Ser Arg Glu Glu Met Thr Lys Asn Gln
        370                 375                 380
Val Ser Leu Thr Cys Leu Val Lys Gly Phe Tyr Pro Ser Asp Ile Ala
385                 390                 395                 400
Val Glu Trp Glu Ser Asn Gly Gln Pro Glu Asn Asn Tyr Lys Thr Thr
                405                 410                 415
Pro Pro Val Leu Asp Ser Asp Gly Ser Phe Phe Leu Tyr Ser Lys Leu
            420                 425                 430
Thr Val Asp Lys Ser Arg Trp Gln Gln Gly Asn Val Phe Ser Cys Ser
            435                 440                 445
Val Met His Glu Ala Leu His Asn His Tyr Thr Gln Lys Ser Leu Ser
        450                 455                 460
Leu Ser Pro Gly Lys
```

<210> SEQ ID NO 42
<211> LENGTH: 1410
<212> TYPE: DNA
<213> ORGANISM: Homo sapiens
<220> FEATURE:
<221> NAME/KEY: CDS
<222> LOCATION: (1)..(1410)

<400> SEQUENCE: 42

| | | | | | | | | | | | | | | | | |
|---|---|---|---|---|---|---|---|---|---|---|---|---|---|---|---|---|
| atg | gct | tgg | gtg | tgg | acc | ttg | cca | ttc | ctg | atg | gca | gct | gcc | caa | agt | 48 |
| Met | Ala | Trp | Val | Trp | Thr | Leu | Pro | Phe | Leu | Met | Ala | Ala | Ala | Gln | Ser | |
| 1 | | | | 5 | | | | | 10 | | | | | 15 | | |
| gtc | cag | gca | gaa | gtg | cag | ctg | gtg | gag | tct | ggg | gga | ggc | gtg | gtc | cag | 96 |
| Val | Gln | Ala | Glu | Val | Gln | Leu | Val | Glu | Ser | Gly | Gly | Gly | Val | Val | Gln | |
| | | | 20 | | | | | 25 | | | | | 30 | | | |
| cct | ggg | agg | tcc | ctg | aga | ctc | tcc | tgt | gca | gcg | tct | gga | ttc | acc | ttc | 144 |
| Pro | Gly | Arg | Ser | Leu | Arg | Leu | Ser | Cys | Ala | Ala | Ser | Gly | Phe | Thr | Phe | |
| | | 35 | | | | | 40 | | | | | 45 | | | | |
| agt | agc | tat | ggc | atg | cac | tgg | gtc | cgc | cag | gct | cca | ggc | aag | ggg | ctg | 192 |
| Ser | Ser | Tyr | Gly | Met | His | Trp | Val | Arg | Gln | Ala | Pro | Gly | Lys | Gly | Leu | |
| | 50 | | | | | 55 | | | | | 60 | | | | | |
| gag | tgg | gtg | gca | att | ata | tgg | tat | gat | gga | agt | aat | aaa | tac | tat | gcg | 240 |
| Glu | Trp | Val | Ala | Ile | Ile | Trp | Tyr | Asp | Gly | Ser | Asn | Lys | Tyr | Tyr | Ala | |
| 65 | | | | | 70 | | | | | 75 | | | | | 80 | |
| gac | tcc | gtg | aag | ggc | cga | ttc | acc | atc | tcc | aga | gac | aat | tcc | aag | aac | 288 |
| Asp | Ser | Val | Lys | Gly | Arg | Phe | Thr | Ile | Ser | Arg | Asp | Asn | Ser | Lys | Asn | |
| | | | | 85 | | | | | 90 | | | | | 95 | | |
| acg | ctg | tat | ctg | caa | atg | aac | agc | ctg | aga | gcc | gag | gac | acg | gct | gtg | 336 |
| Thr | Leu | Tyr | Leu | Gln | Met | Asn | Ser | Leu | Arg | Ala | Glu | Asp | Thr | Ala | Val | |
| | | | 100 | | | | | 105 | | | | | 110 | | | |
| tat | tac | tgt | gcg | agg | cta | tgg | ttc | ggg | gac | tta | gat | gct | ttt | gat | atc | 384 |
| Tyr | Tyr | Cys | Ala | Arg | Leu | Trp | Phe | Gly | Asp | Leu | Asp | Ala | Phe | Asp | Ile | |
| | | | 115 | | | | | 120 | | | | | 125 | | | |
| tgg | ggc | caa | ggg | aca | atg | gtc | acc | gtc | tcc | tca | gcc | tcc | acc | aag | ggc | 432 |
| Trp | Gly | Gln | Gly | Thr | Met | Val | Thr | Val | Ser | Ser | Ala | Ser | Thr | Lys | Gly | |
| | 130 | | | | | 135 | | | | | 140 | | | | | |
| cca | tcg | gtc | ttc | ccc | ctg | gca | ccc | tcc | tcc | aag | agc | acc | tct | ggg | ggc | 480 |
| Pro | Ser | Val | Phe | Pro | Leu | Ala | Pro | Ser | Ser | Lys | Ser | Thr | Ser | Gly | Gly | |
| 145 | | | | | 150 | | | | | 155 | | | | | 160 | |
| aca | gcg | gcc | ctg | ggc | tgc | ctg | gtc | aag | gac | tac | ttc | ccc | gaa | ccg | gtg | 528 |
| Thr | Ala | Ala | Leu | Gly | Cys | Leu | Val | Lys | Asp | Tyr | Phe | Pro | Glu | Pro | Val | |
| | | | | 165 | | | | | 170 | | | | | 175 | | |
| acg | gtg | tcg | tgg | aac | tca | ggc | gcc | ctg | acc | agc | ggc | gtg | cac | acc | ttc | 576 |
| Thr | Val | Ser | Trp | Asn | Ser | Gly | Ala | Leu | Thr | Ser | Gly | Val | His | Thr | Phe | |
| | | | 180 | | | | | 185 | | | | | 190 | | | |
| ccg | gct | gtc | cta | cag | tcc | tca | gga | ctc | tac | tcc | ctc | agc | agc | gtg | gtg | 624 |
| Pro | Ala | Val | Leu | Gln | Ser | Ser | Gly | Leu | Tyr | Ser | Leu | Ser | Ser | Val | Val | |
| | | | 195 | | | | | 200 | | | | | 205 | | | |
| acc | gtg | ccc | tcc | agc | agc | ttg | ggc | acc | cag | acc | tac | atc | tgc | aac | gtg | 672 |
| Thr | Val | Pro | Ser | Ser | Ser | Leu | Gly | Thr | Gln | Thr | Tyr | Ile | Cys | Asn | Val | |
| | 210 | | | | | 215 | | | | | 220 | | | | | |
| aat | cac | aag | ccc | agc | aac | acc | aag | gtg | gac | aag | aga | gtt | gag | ccc | aaa | 720 |
| Asn | His | Lys | Pro | Ser | Asn | Thr | Lys | Val | Asp | Lys | Arg | Val | Glu | Pro | Lys | |
| 225 | | | | | 230 | | | | | 235 | | | | | 240 | |
| tct | tgt | gac | aaa | act | cac | aca | tgc | cca | ccg | tgc | cca | gca | cct | gaa | ctc | 768 |
| Ser | Cys | Asp | Lys | Thr | His | Thr | Cys | Pro | Pro | Cys | Pro | Ala | Pro | Glu | Leu | |
| | | | | 245 | | | | | 250 | | | | | 255 | | |
| ctg | ggg | gga | ccg | tca | gtc | ttc | ctc | ttc | ccc | cca | aaa | ccc | aag | gac | acc | 816 |
| Leu | Gly | Gly | Pro | Ser | Val | Phe | Leu | Phe | Pro | Pro | Lys | Pro | Lys | Asp | Thr | |

```
                    260                 265                 270
ctc atg atc tcc cgg acc cct gag gtc aca tgc gtg gtg gtg gac gtg         864
Leu Met Ile Ser Arg Thr Pro Glu Val Thr Cys Val Val Val Asp Val
        275                 280                 285 agc cac gaa gac cct gag gtc aag ttc aac tgg tac gtg gac ggc gtg         912
Ser His Glu Asp Pro Glu Val Lys Phe Asn Trp Tyr Val Asp Gly Val
    290                 295                 300 gag gtg cat aat gcc aag aca aag ccg cgg gag gag cag tac aac agc         960
Glu Val His Asn Ala Lys Thr Lys Pro Arg Glu Glu Gln Tyr Asn Ser
305                 310                 315                 320 acg tac cgt gtg gtc agc gtc ctc acc gtc ctg cac cag gac tgg ctg        1008
Thr Tyr Arg Val Val Ser Val Leu Thr Val Leu His Gln Asp Trp Leu
            325                 330                 335 aat ggc aag gag tac aag tgc aag gtc tcc aac aaa gcc ctc cca gcc        1056
Asn Gly Lys Glu Tyr Lys Cys Lys Val Ser Asn Lys Ala Leu Pro Ala
                340                 345                 350 ccc atc gag aaa acc atc tcc aaa gcc aaa ggg cag ccc cga gaa cca        1104
Pro Ile Glu Lys Thr Ile Ser Lys Ala Lys Gly Gln Pro Arg Glu Pro
                    355                 360                 365 cag gtg tac acc ctg ccc cca tcc cgg gag gag atg acc aag aac cag        1152
Gln Val Tyr Thr Leu Pro Pro Ser Arg Glu Glu Met Thr Lys Asn Gln
370                 375                 380 gtc agc ctg acc tgc ctg gtc aaa ggc ttc tat ccc agc gac atc gcc        1200
Val Ser Leu Thr Cys Leu Val Lys Gly Phe Tyr Pro Ser Asp Ile Ala
385                 390                 395                 400 gtg gag tgg gag agc aat ggg cag ccg gag aac aac tac aag acc acg        1248
Val Glu Trp Glu Ser Asn Gly Gln Pro Glu Asn Asn Tyr Lys Thr Thr
                405                 410                 415 cct ccc gtg ctg gac tcc gac ggc tcc ttc ttc ctc tat agc aag ctc        1296
Pro Pro Val Leu Asp Ser Asp Gly Ser Phe Phe Leu Tyr Ser Lys Leu
                420                 425                 430 acc gtg gac aag agc agg tgg cag cag ggg aac gtc ttc tca tgc tcc        1344
Thr Val Asp Lys Ser Arg Trp Gln Gln Gly Asn Val Phe Ser Cys Ser
                    435                 440                 445 gtg atg cat gag gct ctg cac aac cac tac acg cag aag agc ctc tcc        1392
Val Met His Glu Ala Leu His Asn His Tyr Thr Gln Lys Ser Leu Ser
    450                 455                 460 ctg tcc ccg ggt aaa tga                                                1410
Leu Ser Pro Gly Lys
465
```

NUCLEIC ACID ENCODING ANTI-IL13 HUMAN ANTIBODIES

RELATED APPLICATIONS

This application is a Continuation of U.S. application Ser. No. 14/044,314, filed Oct. 2, 2013, now U.S. Pat. No. 8,992,916, which is a Divisional of U.S. application Ser. No. 12/975,667 filed Dec. 22, 2010, now U.S. Pat. No. 8,580,260, which is a Divisional of U.S. application Ser. No. 12/091,020 filed Apr. 22, 2008, now U.S. Pat. No. 7,910,708, which is a U.S. National Phase filing of PCT/EP2006/010098 filed Oct. 19, 2006, which claims priority to GB Patent Application 0616666.4 filed Aug. 22, 2006 and GB Patent Application 0521509.0 filed Oct. 21, 2005, the contents of each of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Feb. 20, 2015, is named PAT034582-US_CNT_SEQ_LIST.txt and is 42,362 bytes in size.

FIELD OF USE

The present invention relates to specific binding members, in particular human anti-IL-13 antibody molecules and especially those which neutralize IL-13 activity. It further relates to methods for using anti-IL-13 antibody molecules in diagnosis or treatment of IL-13 related disorders, such as asthma, atopic dermatitis, allergic rhinitis, fibrosis, inflammatory bowel disease and Hodgkin's lymphoma.

BACKGROUND OF THE INVENTION

Interleukin (IL)-13 is a 114 amino acid cytokine with an unmodified molecular mass of approximately 12 kDa [McKenzie, A. N., et al. J Immunol, 1993.150 (12): p. 5436-44, and Minty, A., et al. Nature, 1993.362 (6417): p. 248-50.]. IL-13 is most closely related to IL-4 with which it shares 30% sequence similarity at the amino acid level. The human IL-13 gene is located on chromosome 5q31 adjacent to the IL-4 gene. This region of chromosome 5q contains gene sequences for other Th2 lymphocyte derived cytokines including GM-CSF and IL-5, whose levels together with IL-4 have been shown to correlate with disease severity in asthmatics and rodent models of allergic inflammation [Nakamura, Y., et al. Am J Respir Cell Mol Biol, 1996. 15 (5): p. 680-7, Robinson, D. S., et al. N Engl J Med, 1992.326 (5): p. 298-304, Walker, C., et al. Am J Respir Crit Care Med, 1994. 150 (4): p. 1038-48, Humbert, M., et al. Am J Respir Crit Care Med, 1996, 154 (5): p. 1497-504, Corrigan, C. J. and A. B. Kay Int Arch Allergy Appl Immunol, 1991. 94 (1-4): p. 270-1, Bentley, A. M., et al. Am J Respir Cell Mol Biol, 1993.].

Although initially identified as a Th2 CD4+ lymphocyte derived cytokine, IL-13 is also produced by Th1 CD4+ T-cells, CD8+ T lymphocytes NK cells, and non-T-cell populations such as mast cells, basophils, eosinophils, macrophages, monocytes and airway smooth muscle cells.

IL-13 is reported to mediate its effects through a receptor system that includes the IL-4 receptor a chain (IL-4Rα)-, which itself can bind IL-4 but not IL-13, and at least two other cell surface proteins, IL-13Rα$_1$ and IL-13Rα$_2$ [Murata, T., et al. Int J Hematol, 1999. 69(1): p. 13-20, Andrews, A. L., et al. J Biol Chem, 2002. 277(48): p. 46073-8.]. IL-13Rα$_1$ can bind IL-13 with low affinity, subsequently recruiting IL-4Rα to form a high affinity functional receptor that signals [Miloux, B., et al. FEBS Lett, 1997.401 (2-3): p. 163-6, Hilton, D. J., et al. Proc Natl Acad Sci USA, 1996. 93 (1): p. 497-501]. The Genbank database lists the amino acid sequence and the nucleic acid sequence of IL-13Rα$_1$ as NP 001551 and Y10659 respectively. Studies in STATE (signal transducer and activator of transcription 6)-deficient mice have revealed that IL-13, in a manner similar to IL-4, signals by utilizing the JAK-STAT6 pathway [Kuperman, D., et al. J Exp Med, 1998. 187 (6): p. 939-48, Nelms, K., et al. Annu Rev Immunol, 1999.17: p. 701-38.]. IL-13Rα$_2$ shares 37% sequence identity with IL-13Rα$_1$ at the amino acid level and binds IL-13 with high affinity [Zhang, J. G., et al. J Biol Chem, 1997.272 (14): p. 9474-80, Caput, D., et al. J Biol Chem, 1996.271 (28): p. 16921-6.]. However, IL-13Rα$_2$ has a shorter cytoplasmic tail that lacks known signaling motifs. Cells expressing IL-13Rα$_2$ are not responsive to IL-13 even in the presence of IL-4Rα[Kawakami, K., et al. Blood, 2001.97 (9): p. 2673-9]. It is postulated, therefore, that IL-13Rα$_2$ acts as a decoy receptor regulating IL-13 but not IL-4 function. This is supported by studies in IL-13Rα$_2$ deficient mice whose phenotype was consistent with increased responsiveness to IL-13 [Wood, N., et al. J Exp Med, 2003.197 (6): p. 703-709, Chiaramonte, M. G., et al. J Exp Med, 2003.197 (6): p. 687-701]. The Genbank database lists the amino acid sequence and the nucleic acid sequence of IL-13Rα$_2$ as NP000631 and Y08768 respectively.

SUMMARY OF THE INVENTION

An embodiment of the invention herein provides an isolated human or humanized antibody or functional fragment thereof with an antigen-binding region that is specific for target protein IL-13 and the antibody or functional fragment thereof binds to IL-13. In a related embodiment, the binding to IL-13 is determined at least by cell surface IL-13 receptor binding preventing inflammatory mediator release.

In still another embodiment, the invention provides an isolated antigen-binding region of an antibody or functional fragment thereof. In certain embodiments, the isolated antigen-binding region includes an H-CDR3 region having an amino acid sequence selected from SEQ ID NOs: 9-10, and conservative variants thereof. As described herein, the conservative variants include amino acid residues in any of the amino acid sequences identified. In a related embodiment, the isolated antigen-binding region is an H-CDR2 region having the amino acid sequence of SEQ ID NO: 8, and conservative variants thereof. In another related embodiment, the isolated antigen-binding region is an H-CDR1 region having an amino acid sequence selected from SEQ ID NO: 6-7, and conservative variants thereof.

In another embodiment, the isolated antigen-binding region is an L-CDR3 region having an amino acid sequence selected from SEQ ID NOs: 20-22, and conservative variants thereof. In still another related embodiment, the isolated antigen-binding region is an L-CDR1 region having an amino acid sequence selected from SEQ ID NOs: 16-18, and conservative variants thereof. In yet another related embodiment, the isolated antigen-binding region is an L-CDR2 region having the amino acid sequence of SEQ ID NO: 19, and conservative variants thereof.

In certain embodiments, the isolated antigen-binding region is a variable light chain having an amino acid sequence selected from SEQ ID 16-22, and conservative variants thereof.

In another embodiment, the isolated antigen-binding region is a heavy chain having an amino acid sequence selected from one to three of SEQ ID 6-10, and a sequence having at least 60, 70, 80, 90 or 95 percent sequence identity in the CDR regions with the CDR regions having SEQ ID NOs: 6-10. In a related embodiment, the isolated antigen-binding region is a light chain having an amino acid sequence selected from one to three of SEQ ID NOs: 16-22, and a sequence having at least 60, 70, 80, 90 or 95 percent sequence identity in the CDR regions with the CDR regions having SEQ ID NOs: 16-22.

In a certain embodiment, the isolated antibody is an IgG. In another embodiment, the isolated antibody is an IgG1 or an IgG4.

In yet another embodiment, the invention provides an isolated human or humanized antibody or functional fragment thereof, having an antigen-binding region that is specific for an epitope of IL-13, and the antibody or functional fragment binds to IL-13 surface receptors on a cell. In a related embodiment, the invention provides an isolated human or humanized antibody or functional fragment thereof, having an antigen-binding region that is specific for an epitope of target IL-13, and the epitope contains one or more amino acid residues of amino acid residues 1-112 of target IL-13. In a related embodiment, the epitope is a conformational epitope.

In yet another embodiment, the antibody or functional fragment is a Fab or scFv antibody fragment. In a related embodiment, the isolated antibody is an IgG. In another related embodiment, the isolated antibody is an IgG1 or an IgG4.

In another embodiment, the invention provides a pharmaceutical composition having at least one of any of the above antibodies or functional fragments or conservative variants, and a pharmaceutically acceptable carrier or excipient therefor.

In still another embodiment, the invention provides for a transgenic animal carrying a gene encoding any of the above antibodies or functional fragments thereof.

In certain embodiments, the invention provides a method for treating a disorder or condition associated with the presence of a cell having a receptor target for IL-13. The method involves administering to a subject in need thereof an effective amount of any of the above pharmaceutical compositions. In a related embodiment, the disorder or condition to be treated is a respiratory disorder.

In another embodiment, the disorder or condition to be treated is bronchial asthma, which is a common persistent inflammatory disease of the lung characterised by airways hyper-responsiveness (AHR), mucus overproduction, fibrosis and raised serum IgE levels. Li et al, Abstract for poster submitted at The American Thoraics Society Annual Meeting, 2003, Seattle, reported affects of a neutralising antimouse IL-13 antibody in a chronic mouse model of asthma.

In another embodiment, the disorder or condition to be treated is Chronic Obstructive Pulmonary Disease (COPD). Zheng et al J Clin Invest, 2000.106 (9): p. 1081-93, have demonstrated that over expression of IL-13 in the mouse lung caused emphysema, elevated mucus production and inflammation, reflecting aspects of human COPD. mRNA levels of IL-13 have been shown to be higher in autopsy tissue samples from subjects with a history of COPD when compared to lung samples from subjects with no reported lung disease (J. Elias, Oral communication at American Thoracic Society Annual Meeting 2002). In another study, raised levels of IL-13 were demonstrated by immunohistochemistry in peripheral lung sections from COPD patients [Wardlaw, A. J., Clin Med, 2001.1 (3): p. 214-8.].

In another embodiment, the disorder or condition to be treated is selected from other inflammatory or obstructive airways diseases and conditions such as acute lung injury (ALI), acute/adult respiratory distress syndrome (ARDS), dyspnea, allergic airway inflammation, small airway disease, lung carcinoma, acute chest syndrome in patients with sickle cell disease and pulmonary hypertension, as well as exacerbation of airways hyperreactivity consequent to other drug therapy, in particular other inhaled drug therapy.

In another embodiment, the disorder or condition to be treated is bronchitis of whatever type or genesis including, e.g., acute, arachidic, catarrhal, croupus, chronic or phthinoid bronchitis.

In another embodiment, the disorder or condition to be treated includes pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

In another embodiment, the disorder or condition to be treated is selected from atopic rhinitis (hay fever), allergic dermatitis (eczema) and chronic sinusitis. Raised levels of IL-13 have been measured in human subjects with atopic rhinitis (hay fever), allergic dermatitis (eczema) and chronic sinusitis. For example levels of IL-13 were found to be higher in bronchial biopsies, sputum and broncho-alveolar lavage (BAL) cells from asthmatics compared to control subjects [Humbert, M., et al. J Allergy Clin Immunol, 1997.99 (5): p. 657-65, Kotsimbos, T. C., P. Ernst, and Q. A. Hamid, Proc Assoc Am Physicians, 1996. 108 (5): p. 368-73, Komai-Koma, M., F. Y. Liew, and P. C. Wilkinson, J Immunol, 1995.155 (3): p. 1110-6, Naseer, T., et al. Am J Respir Crit Care Med, 1997].

In another embodiment, the disorder or condition to be treated is selected from other inflammatory conditions of the skin, for example, psoriasis or lupus erythematosus.

In another embodiment, the disorder or condition to be treated is inflammatory bowel disease, such as ulcerative colitis and Crohn's disease. Heller et al. (2002) Immunity, 17 (5): 629-38, report that neutralisation of IL-13 by administration of soluble IL-13Ra2 ameliorated colonic inflammation in a murine model of human ulcerative colitis. Correspondingly, IL-13 expression was higher in rectal biopsy specimens from ulcerative colitis patients when compared to controls.

In another embodiment, the disorder or condition to be treated is selected from other fibrotic conditions, such as systemic sclerosis, pulmonary fibrosis, idiopathic pulmonary fibrosis or fibroid lung. Increased levels of IL-13 have been measured in the serum of patients with systemic sclerosis [Hasegawa, M., et al. J Rheumatol, 1997. 24 (2): p. 328-32] and in BAL samples from patients affected with other forms of pulmonary fibrosis [Hancock, A., et al. Am J Respir Cell Mol Biol, 1998].

In another embodiment, the disorder or condition to be treated is liver fibrosis. Specific inhibition of IL-13 by administration of soluble IL-13Ra2 or IL-13 gene disruption, but not ablation of IL-4 production prevented fibrogenesis in the liver [Fallon, P. G., et al. J Immunol, 2000.164 (5): p. 2585-91, Chiaramonte, M. G., et al. J Clin Invest, 1999.104 (6): p. 777-85, Chiaramonte, M. G., et al. Hepatology, 2001. 34(2): p. 273-82.].

In another embodiment, the disorder or condition to be treated is Hodgkin's disease. Hodgkin's disease is unusual among malignancies in that the neoplastic Reed-Sternberg cell, often derived from B-cells, make up only a small proportion of the clinically detectable mass. Hodgkin's disease-derived cell lines and primary ReedSternberg cells frequently express IL-13 and its receptor [Skinnider, B. F., et al. Blood, 2001. 97(1): p. 250-5]. As IL-13 promotes cell survival and proliferation in normal B-cells, it was proposed that IL-13 could act as a growth factor for Reed-Sternberg cells. Skinnider et al. have demonstrated that neutralising antibodies against IL-13 can inhibit the growth of Hodgkin's disease-derived cell lines in vitro [Kapp, U., et al. J Exp Med, 1999. 189 (12): p. 1939-46.]. This finding suggested that Reed-Sternberg cells might enhance their own survival by an IL-13 autocrine and paracrine cytokine loop. Consistent with this hypothesis, raised levels of IL-13 have been detected in the serum of some Hodgkin's disease patients when compared to normal controls [Fiumara, P., F. Cabanillas, and A. Younes, Blood, 2001. 98 (9): p. 2877-8.]. IL-13 inhibitors may therefore prevent disease progression by inhibiting proliferation of malignant Reed-Sternberg cells.

In another embodiment, the disorder or condition to be treated is tumour recurrence or metastasis Inhibition of IL-13 has been shown to enhance anti-viral vaccines in animal models and may be beneficial in the treatment of HIV and other infectious diseases [Ahlers, J. D., et al. Proc Natl Acad Sci USA, 2002]. Many human cancer cells express immunogenic tumour specific antigens. However, although many tumours spontaneously regress, a number evade the immune system (immunosurveillance) by suppressing T-cell mediated immunity. Terabe et al. Nat Immunol, 2000.1 (6): p. 515-20, have demonstrated a role of IL-13 in immunosuppression in a mouse model in which tumours spontaneously regress after initial growth and then recur. Specific inhibition of IL-13, with soluble IL-13Ra2, protected these mice from tumour recurrence. Terabe et al went on to show that IL-13 suppresses the differentiation of tumour specific CD8+ cytotoxic lymphocytes that mediate anti-tumour immune responses.

In another embodiment, the disorder or condition to be treated is a respiratory viral infection, which exacerbates underlying chronic conditions such as asthma, chronic bronchitis, COPD, otitis media, and sinusitis. The respiratory viral infection treated may be associated with secondary bacterial infection, such as otitis media, sinusitis or pneumonia.

In another embodiment, the disorder or condition to be treated is selected from other diseases or conditions, in particular diseases or conditions having an inflammatory component, for example, diseases of the bone and joints including rheumatoid arthritis, psoriatic arthritis, and other diseases such as atherosclerosis, multiple sclerosis, and acute and chronic allograft rejection, e.g. following transplantation of heart, kidney, liver, lung or bone marrow.

In another embodiment, the disorder or condition to be treated is endotoxic shock, glomerulonephritis, cerebral and cardiac ischemia, Alzheimer's disease, cystic fibrosis, virus infections and the exacerbations associated with them, acquired immune deficiency syndrome (AIDS), multiple sclerosis (MS), *Helicobacter pylori* associated gastritis, and cancers, particularly the growth of ovarian cancer.

In another embodiment, the disorder or condition to be treated is the symptoms caused by viral infection in a human which is caused by the human rhinovirus, other enterovirus, coronavirus, herpes viruses, influenza virus, parainfluenza virus, respiratory syncytial virus or an adenovirus.

Treatment in accordance with the present invention may be symptomatic or prophylactic.

The effectiveness of an agent of the invention in inhibiting inflammatory conditions, for example in inflammatory airways diseases, may be demonstrated in an animal model, e.g. mouse, rat or rabbit model, of airway inflammation or other inflammatory conditions, for example as described by Wada et al, *J. Exp. Med* (1994) 180:1135-40; Sekido et al, *Nature* (1993) 365:654-57; Modelska et al., *Am. J. Respir. Crit. Care. Med* (1999) 160:1450-56; and Laffon et al (1999) *Am. J. Respir. Grit. Care Med.* 160:1443-49.

In yet another embodiment, the invention provides a method for identifying a cell having a receptor for IL-13. This method involves contacting the cell with any of the above antibodies or antibody fragments further having a detectable label. The label is radioactive, fluorescent, magnetic, paramagnetic, or chemiluminescent. The method further can involve any of the above imaging or separating the labeled cell.

In another embodiment, any of the above human or humanized antibodies or antibody fragments are synthetic.

In another embodiment, the invention provides a pharmaceutical composition and an additional therapeutic agent.

The additional therapeutic agent can be selected from the group consisting of anti-inflammatory, bronchodilatory, antihistamine or anti-tussive drug substances, particularly in the treatment of obstructive or inflammatory airways diseases such as those mentioned hereinbefore, for example as potentiators of therapeutic activity of such drugs or as a means of reducing required dosaging or potential side effects of such drugs. A therapeutic agent of the invention may be mixed with the other drug substance in a fixed pharmaceutical composition or it may be administered separately, before, simultaneously with or after the other drug substance. Accordingly the invention includes a combination of an agent of the invention as hereinbefore described with an anti-inflammatory, bronchodilatory, antihistamine or anti-tussive drug substance, said agent of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTB4 antagonists such as BIIL 284, CP-195543, DPC11870, LTB4 ethanolamide, LY 293111, LY 255283, CGS025019C, CP-195543, ONO-4057, SB 209247, SC-53228 and those described in U.S. Pat. No. 5,451,700; LTD4 antagonists such include montelukast, pranlukast, zafirlukast, accolate, SR2640, Wy-48,252, ICI 198615, MK-571, LY-171883, Ro 24-5913 and L-648051; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (*Asta Medica*), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; $A_{2A}$ agonists such as those described in EP 1052264, EP 1241176, EP 409595A2, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, and WO 03/086408; and $A_{2B}$ antagonists such as those described in WO 02/42298.

Suitable bronchodilatory drugs include anticholinergic or antimuscarinic agents, in particular ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, WO 01/04118, WO 02/00652, WO 02/51841, WO 02/53564, WO 03/00840, WO 03/33495, WO 03/53966, WO 03/87094, WO 04/018422 and WO 04/05285; and beta-2 adrenoceptor agonists such as albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula I of WO 00/75114, which document is incorporated herein by reference, preferably compounds of the Examples thereof, especially a compound of formula

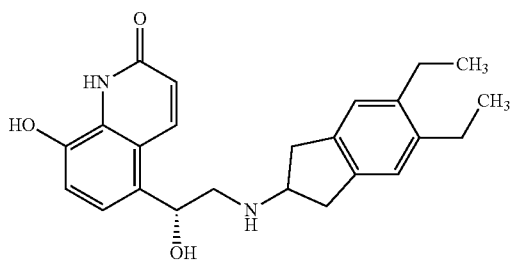 [SMILES: CCc1cc2c(cc1CC)CC(NC[C@H](O)c1ccc(O)c3[nH]c(=O)ccc13)C2]

i.e., (5-[(R)-2-(5,6-Diethyl-indan-2-ylamino)-1-hydroxyethyl]-8-hydroxy-1H-quinolin-2-one) and pharmaceutically acceptable salts thereof, as well as compounds (in free or salt or solvate form) of formula I of WO 04/16601, and also compounds of EP 1440966, JP 05025045, WO 93/18007, WO 99/64035, US 2002/0055651, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083, WO 04/80964, EP1460064, WO 04/087142, WO 04/089892, EP 01477167, US 2004/0242622, US 2004/0229904, WO 04/108675, WO 04/108676, WO 05/033121, WO 05/040103 and WO 05/044787.

Suitable dual anti-inflammatory and bronchodilatory drugs include dual beta-2 adrenoceptor agonist/muscarinic antagonists such as those disclosed in US 2004/0167167, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in JP 2004107299, WO 03/099807 and WO 04/026841.

Combinations of therapeutic agents of the invention and anticholinergic or antimuscarinic agents, steroids, beta-2 agonists, PDE4 inhibitors, dopamine receptor agonists, LTD4 antagonists or LTB4 antagonists may also be used. Other useful combinations of agents of the invention with anti-inflammatory drugs are those with other antagonists of chemokine receptors, e.g. CCR-1, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]-methyl]-tetrahydro-N,N-dimethyl-2H-pyran-4-aminium chloride (TAK-770), CCR-5 antagonists described in U.S. Pat. No. 6,166,037 (particularly claims 18 and 19), WO 0066558 (particularly claim 8), WO 0066559 (particularly claim 9), WO 04/018425 and WO 04/026873.

The additional therapeutic agent may also be selected from the group consisting of other cytokine binding molecules, particularly antibodies of other cytokines, in particular a combination with an anti-IL4 antibody, such as described in PCT/EP2005/00836, an anti-IgE antibody, such as Xolair®, an anti-IL31 antibody, an anti-IL31R antibody, an anti-TSLP antibody, an anti-TSLP receptor antibody, an anti-endoglin antibody, an anti-IL1b antibody or another anti-IL13 antibody, such as described in WO05/007699.

In a certain embodiment, the invention provides an antibody having a first amino acid sequence which is a heavy chain selected from one to three of SEQ ID NOs: 6-10, and a sequence having at least 60, 70, 80, 90 or 95 percent sequence identity in the CDR regions with the CDR regions having SEQ ID NOs: 6-10; and a second amino acid sequence which is a light chain selected from one to three of SEQ ID NOs: 16-22, and a sequence having at least 60, 70, 80, 90 or 95 percent sequence identity in the CDR regions with the CDR regions shown in SEQ ID NOs: 16-22.

In still another embodiment, the invention provides an immunoconjugate made out of a first component which is an antibody or fragment thereof and a second component having a second amino acid sequence. For example, the immunoconjugate is a cytotoxin, or the immunoconjugate is a binding protein or antibody having a binding specificity for a target that is different from IL-13.

In certain embodiments, the invention provides for a bispecific antibody.

In another embodiment, the invention provides a kit having an antibody or antibody fragment thereof. In some embodiments, the kit further contains a pharmaceutically acceptable carrier or excipient therefore. In other related embodiments, the antibody in the kit is present in a unit dose. In yet another related embodiment, the kit includes instructions for use in administering to a subject.

DETAILED DESCRIPTION OF THE INVENTION

The present invention relates to isolated antibodies, particularly human antibodies, that bind specifically to IL-13 and that inhibit functional properties of IL-13. In certain embodiments, the antibodies of the invention are derived from particular heavy and light chain sequences and/or comprise particular structural features such as CDR regions comprising particular amino acid sequences. The invention provides isolated antibodies, methods of making such antibodies, immunoconjugates and bispecific molecules comprising such antibodies and pharmaceutical compositions containing the antibodies, immunconjugates or bispecific molecules of the invention. The invention also relates to methods of using the antibodies to inhibit a disorder or condition associated with the presence of cell receptor target IL-13, for example, in the treatment of an inflammatory or allergic condition, particularly an inflammatory or obstructive airways disease.

In order that the present invention may be more readily understood, certain terms are first defined. Additional definitions are set forth throughout the detailed description.

The term 'interleukin-13' or 'IL-13' is, except where context dictates otherwise, reference to human IL-13. The present invention provides antibodies to human IL-13, especially human antibodies, that are cross-reactive with non-human primate IL-13, including cynomolgus and rhesus monkey IL-13. Antibodies in accordance with some embodiments of the present invention recognise a variant of IL-13 in which the arginine residue at amino acid position 130 is replaced by glutamine. In other aspects and embodiments the present invention provides specific binding members against murine IL-13, specifically mouse IL-13.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and capable of the transmission of such a signal across the plasma membrane of a cell. An example of a "cell surface receptor" of the present invention is the IL-13 receptor to which the IL-13 protein molecule binds.

The term "antibody" as referred to herein includes whole antibodies and any antigen binding fragment (i. e., "antigen-binding portion") or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is, composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antigen portion"), as used herein, refers to one or more fragments of an antibody that retain the ability to specifically bind to an antigen (e.g., IL-13). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, $C_L$ and CH1 domains; a F(ab)$_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated complementarity determining region (CDR).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., 1988 Science 242:423-426; and Huston et al., 1988 Proc. Natl. Acad. Sci. 85:5879-5883). Such single chain antibodies are also intended to be encompassed within the term "antigen-binding portion" of an antibody. These antibody fragments are obtained using conventional techniques known to those of skill in the art, and the fragments are screened for utility in the same manner as are intact antibodies.

An "isolated antibody", as used herein, refers to an antibody that is substantially free of other antibodies having different antigenic specificities (e.g., an isolated antibody that specifically binds IL-13 is substantially free of antibodies that specifically bind antigens other than IL-13). An isolated antibody that specifically binds IL-13 may, however, have cross-reactivity to other antigens, such as IL-13 molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies of the invention may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM, IgE, IgG such as IgG1 or IgG4) that is encoded by the heavy chain constant region genes.

The phrases "an antibody recognizing an antigen" and "an antibody specific for an antigen" are used interchangeably herein with the term "an antibody which binds specifically to an antigen."

As used herein, an antibody that "specifically binds to human IL-13" is intended to refer to an antibody that binds to human IL-13 with a $K_D$ of $5 \times 10^{-9}$ M or less. An antibody that "cross-reacts with an antigen other than human IL-13" is intended to refer to an antibody that binds that antigen with a $5 \times 10^{-9}$ M or less. An antibody that "does not cross-react with a particular antigen" is intended to refer to an antibody that binds to that antigen, with a $K_D$ of $1.5 \times 10^{-8}$ M or greater, or a $K_D$ of $5 - 10 \times 10^{-8}$ M or $1 \times 10^{-7}$ M or greater. In certain embodiments, such antibodies that do not cross-react with the antigen exhibit essentially undetectable binding against these proteins in standard binding assays.

As used herein, an antibody that "inhibits binding of IL-13 to the IL-13 receptor" refers to an antibody that inhibits IL-13 binding to the receptor with a KD of 5 nM or less.

As used herein, an antibody that "inhibits inflammatory mediator release" is intended to refer to an antibody that inhibits IL-13 induced eotaxin release from human lung fibroblasts with an $IC_{50}$ less than 10 nM, 5 nM, 2.5 nM, 1.0 nM, 0.5 nM, or less.

The term "$K_{assoc}$" or "$K_a$", as used herein, is intended to refer to the association rate of a particular antibody-antigen interaction, whereas the term "$K_{dis}$" or "$K_D$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a Biacore® system.

As used herein, the term "high affinity" for an IgG antibody refers to an antibody having a $K_D$ of $10^{-8}$ M or less, $10^{-9}$ M or less, or $10^{-10}$ M or less for a target antigen.

As used herein, the term "subject" includes any human or nonhuman animal. The term "nonhuman animal" includes all vertebrates, e.g., mammals and non-mammals, such as nonhuman primates, sheep, dogs, cats, horses, cows chickens, amphibians, reptiles, etc.

Various aspects of the invention are described in further detail in the following subsections.

Standard assays to evaluate the binding ability of the antibodies toward IL-13 of various species are known in the art, including for example, ELISAs, western blots and RIAs. Suitable assays are described in detail in the Examples. The binding kinetics (e.g., binding affinity) of the antibodies also can be assessed by standard assays known in the art, such as by Biacore analysis. Assays to evaluate the effects of the antibodies on functional properties of IL-13 are described in further detail in the Examples.

Accordingly, an antibody that "inhibits" one or more of these IL-13 functional properties (e.g., biochemical, immunochemical, cellular, physiological or other biological activities, or the like) as determined according to methodologies known to the art and described herein, will be understood to relate to a statistically significant decrease in the particular activity relative to that seen in the absence of the antibody (e.g., or when a control antibody of irrelevant specificity is present). An antibody that inhibits IL-13 activity effects such a statistically significant decrease by at least 10% of the measured parameter, by at least 50%, 80% or 90%, and in certain embodiments an antibody of the invention may inhibit greater than 95%, 98% or 99% of IL-13 functional activity.

Monoclonal Antibodies

Antibodies of the invention are the human monoclonal antibodies, isolated and structurally characterized as described, in Examples 1-5. The $V_H$ amino acid sequences of the antibodies are shown in SEQ ID NOs: 6-10 respectively. The $V_L$ amino acid sequences of the antibodies are shown in SEQ ID NOs: 16-22 respectively. Other antibodies of the invention include amino acids that have been mutated, yet have at least 60, 70, 80, 90 or 95 percent identity in the CDR regions with the CDR regions depicted in the sequences described above.

Since each of these antibodies can bind to IL-13, the $V_H$ and $V_L$ sequences can be "mixed and matched" to create other anti-IL-13 binding molecules of the invention. IL-13 binding of such "mixed and matched" antibodies can be tested using the binding assays described above and in the Examples (e.g., ELISAs). When $V_H$ and $V_L$ chains are mixed and matched, a $V_H$ sequence from a particular $V_H/V_L$ pairing should be replaced with a structurally similar $V_H$ sequence. Likewise, a $V_L$ sequence from a particular $V_H/V_L$ pairing should be replaced with a structurally similar $V_L$ sequence. The $V_H$ and $V_L$ sequences of the antibodies of the present invention are particularly amenable for mixing and matching, since these antibodies use $V_H$ and $V_L$ sequences derived from the same germline sequences and thus exhibit structural similarity.

In another aspect, the invention provides antibodies that comprise the heavy chain and light chain CDR's, CDR2s and CDR3s of the antibodies, or combinations thereof. The amino acid sequences of the V$_H$ CDR1s of the antibodies are shown in SEQ ID NOs: 6-7. The amino acid sequence of the V$_H$ CDR2s of the antibodies is shown by SEQ ID NO: 8. The amino acid sequences of the V$_H$ CDR3s of the antibodies are shown in SEQ ID NOs: 9-10.

The amino acid sequences of the V$_L$ CDR1s of the antibodies are shown in SEQ ID NOs: 16-18. The amino acid sequences of the V$_L$ CDR2s of the antibodies is shown in SEQ ID NO: 19. The amino acid sequences of the V$_L$ CDR3s of the antibodies are shown in SEQ ID NOs: 20-22. The CDR regions are delineated using the Kabat system (Kabat, E. A., et al., 1991 Sequences of Proteins of Immunological Interest, Fifth Edition, U.S. Department of Health and Human Services, NIH Publication No. 91-3242).

Given that each of these antibodies can bind to IL-13 and that antigen-binding specificity is provided primarily by the CDR1, 2 and 3 regions, the V$_H$ CDR1, 2 and 3 sequences and V$_L$ CDR1, 2 and 3 sequences can be "mixed and matched" (i.e., CDRs from different antibodies can be mixed and match, although each antibody must contain a V$_H$ CDR1, 2 and 3 and a V$_L$ CDR1, 2 and 3) to create other anti-IL-13 binding molecules of the invention. IL-13 binding of such "mixed and matched" antibodies can be tested using the binding assays described above and in the Examples (e.g., ELISAs). When V$_H$ CDR sequences are mixed and matched, the CDR1, CDR2 and/or CDR3 sequence from a particular V$_H$ sequence should be replaced with a structurally similar CDR sequence(s). Likewise, when V$_L$ CDR sequences are mixed and matched, the CDR1, CDR2 and/or CDR3 sequence from a particular V$_L$ sequence should be replaced with a structurally similar CDR sequence(s). It will be readily apparent to the ordinarily skilled artisan that novel V$_H$ and V$_L$ sequences can be created by substituting one or more V$_H$ and/or V$_L$ CDR region sequences with structurally similar sequences from the CDR sequences shown herein for monoclonal antibodies of the present invention.

An isolated monoclonal antibody, or antigen binding portion thereof has: a heavy chain variable region CDR1 comprising an amino acid sequence selected from the group consisting of SEQ ID NOs: 6-7; a heavy chain variable region CDR2 comprising an amino acid sequence of SEQ ID NO: 8; a heavy chain variable region CDR3 comprising an amino acid sequence selected from the group consisting of SEQ ID NOs: 9-10; a light chain variable region CDR1 comprising an amino acid sequence selected from the group consisting of SEQ ID NOs: 16-18; a light chain variable region CDR2 comprising an amino acid sequence of SEQ ID NO: 19; and a light chain variable region CDR3 comprising an amino acid sequence selected from the group consisting of SEQ ID NOs: 20-22; wherein the antibody specifically binds IL-13.

In a certain embodiment, the antibody consists of: a heavy chain variable region CDR1 comprising SEQ ID NO: 6; a heavy chain variable region CDR2 comprising SEQ ID NO: 8; a heavy chain variable region CDR3 comprising SEQ ID NO: 9; a light chain variable region CDR1 comprising SEQ ID NO: 16; a light chain variable region CDR2 comprising SEQ ID NO: 19; and a light chain variable region CDR3 comprising SEQ ID NO: 20.

In another embodiment, the antibody consists of: a heavy chain variable region CDR1 comprising SEQ ID NO: 7; a heavy chain variable region CDR2 comprising SEQ ID NO: 8; a heavy chain variable region CDR3 comprising SEQ ID NO: 10; a light chain variable region CDR1 comprising SEQ ID NO: 17; a light chain variable region CDR2 comprising SEQ ID NO: 19; and a light chain variable region CDR3 comprising SEQ ID NO: 21.

In yet another embodiment, the antibody consists of: a heavy chain variable region CDR1 comprising SEQ ID NO: 7; a heavy chain variable region CDR2 comprising SEQ ID NO: 8; a heavy chain variable region CDR3 comprising SEQ ID NO: 10; a light chain variable region CDR1 comprising SEQ ID NO: 18; a light chain variable region CDR2 comprising SEQ ID NO: 19; and a light chain variable region CDR3 comprising SEQ ID NO: 22.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the gennline immunoglobulin gene.

Homologous Antibodies

In yet another embodiment, an antibody of the invention has heavy and light chain variable regions having amino acid sequences that are homologous to the amino acid sequences of the antibodies described herein, and wherein the antibodies retain the desired functional properties of the anti-IL-13 antibodies of the Invention.

For example, the invention provides an isolated monoclonal antibody, or antigen binding portion thereof, comprising a heavy chain variable region and a light chain variable region, wherein: the heavy chain variable region comprises an amino acid sequence that is at least 80% homologous to an amino acid sequence selected from the group consisting of SEQ ID NOs: 6-10; the light chain variable region comprises an amino acid sequence that is at least 80% homologous to an amino acid sequence selected from the group consisting of SEQ ID NOs: 16-22; the antibody specifically binds to IL-13, and the antibody exhibits at least one of the following functional properties: the antibody inhibits binding IL-13 protein to the IL-13 receptor or the antibody inhibits IL-13 receptor binding preventing or ameliorating an inflammatory or allergic condition, particularly an inflammatory or obstructive airways disease, or the antibody inhibits IL-13 receptor binding preventing or ameliorating asthma or the antibody inhibits IL-13 receptor binding preventing or ameliorating COPD.

In various embodiments, the antibody may exhibit one or more, two or more, or three of the functional properties discussed above. The antibody can be, for example, a human antibody, a humanized antibody or a chimeric antibody.

In other embodiments, the $V_H$ and/or $V_L$ amino acid sequences may be 60%, 70%, 80%, 90%, 95%, 96%, 97%, 98% or 99% homologous to the sequences set forth above. An antibody having $V_H$ and $V_L$ regions having high (i. e., 80% or greater) homology to the $V_H$ and $V_L$ regions of SEQ ID NOs: 6-10 and 16-22 respectively, can be obtained by mutagenesis (e.g., site-directed or PCR-mediated mutagenesis) of nucleic acid molecules encoding SEQ ID NOs: 6-10 and/or 16-22, followed by testing of the encoded altered antibody for retained function (i. e., the functions set forth above) using the functional assays described herein.

As used herein, the percent homology between two amino acid sequences is equivalent to the percent identity between the two sequences. The percent identity between the two sequences is a function of the number of identical positions shared by the sequences (i. e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol, Biol. 48:444-453, 1970) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al., 1990 J. Mol. Biol. 215:403-10. BLAST protein searches can be performed with the XBLAST program, score=50, word-length=3 to obtain amino acid sequences homologous to the antibody molecules of the invention. To obtain gapped alignments for comparison purposes, Gapped BLAST can be utilized as described in Altschul et al., 1997 Nucleic Acids Res. 25(17):3389-3402. When utilizing BLAST and Gapped BLAST programs, the default parameters of the respective programs (e.g., XBLAST and NBLAST) can be used. See www.ncbi.nhn.nih.gov.

Antibodies with Conservative Modifications

In certain embodiments, an antibody of the invention has a heavy chain variable region consist of CDR1, CDR2, and CDR3 sequences and a light chain variable region consisting of CDR1, CDR2, and CDR3 sequences, wherein one or more of these CDR sequences have specified amino acid sequences based on the antibodies described herein or conservative modifications thereof, and wherein the antibodies retain the desired functional properties of the anti-IL-13 antibodies of the invention. Accordingly, the invention provides an isolated monoclonal antibody, or antigen binding portion thereof, consisting of a heavy chain variable region consisting of CDR1, CDR2, and CDR3 sequences and a light chain variable region consisting of CDR1, CDR2, and CDR3 sequences, wherein: the heavy chain variable regions of CDR1 is sequences consisting of amino acid sequences selected from the group consisting of amino acid sequences of SEQ ID NOs: 6-7, and conservative modifications thereof; the heavy chain variable region of CDR2 is a sequence consisting of an amino acid sequence of SEQ ID NO: 8, and conservative modifications thereof; the heavy chain variable region of CDR3 is sequences consisting of amino acid sequences selected from the group consisting of amino acid sequences of SEQ ID NOs: 9-10, and conservative modifications thereof; the light chain variable regions of CDR1 is sequences consisting of amino acid sequences selected from the group consisting of amino acid sequences of SEQ ID NOs: 16-18, and conservative modifications thereof; the light chain variable regions of CDR2 is a sequence consisting of an amino acid sequence of SEQ ID NO: 19, and conservative modifications thereof; the light chain variable regions of CDR3 is sequences consisting of amino acid sequences selected from the group consisting of amino acid sequences of SEQ ID NOs: 20-22, and conservative modifications thereof; the antibody specifically binds to IL-13; and the antibody inhibits IL-13 receptor binding preventing inflammatory mediator release.

In various embodiments, the antibody may exhibit one or more, two or more, or three or more of the functional properties listed discussed above. Such antibodies can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis.

Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family, and the altered antibody can be tested for retained function using the functional assays described herein.

Antibodies that Bind to the Same Epitope as Anti-IL-13 Antibodies of the Invention In another embodiment, the invention provides antibodies that bind to the same epitope as do the various anti-IL-13 antibodies of the invention provided herein. Such additional antibodies can be identified based on their ability to cross-compete (e.g., to competitively inhibit the binding of, in a statistically significant manner) with other antibodies of the invention in standard IL-13 binding assays. The ability of a test antibody to inhibit the binding of antibodies of the present invention to human IL-13 demonstrates that the test antibody can compete with that antibody for binding to human IL-13; such an antibody may, according to non-limiting theory, bind to the same or a related (e.g., a structurally similar or spatially proximal) epitope on human IL-13 as the antibody with which it competes. In a certain embodiment, the antibody that binds to the same epitope on human IL-13 as the antibodies of the present invention is a human monoclonal antibody. Such human monoclonal antibodies can be prepared and isolated as described in the Examples.

Engineered and Modified Antibodies

An antibody of the invention further can be prepared using an antibody having one or more of the $V_H$ and/or $V_L$ sequences shown herein as starting material to engineer a modified antibody, which modified antibody may have altered properties from the starting antibody. An antibody can be engineered by modifying one or more residues within one or both variable regions (i. e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad. See. U.S.A. 86:10029-10033; U.S. Pat. No. 5,225,539 to winter, and U.S. Pat. Nos. 5,530,101; 5,585,089; 5,693,762 and 6,180,370 to Queen et al.)

Accordingly, another embodiment of the invention pertains to an isolated monoclonal antibody, or antigen binding portion thereof, comprising a heavy chain variable region comprising CDR1 sequences having an amino acid sequence selected from the group consisting of SEQ ID NOs: 6-7; CDR2 sequences having an amino acid sequence of SEQ ID NO: 8; CDR3 sequences having an amino acid sequence selected from the group consisting of SEQ ID NOs: 9-10, respectively; and a light chain variable region having CDR1 sequences having an amino acid sequence selected from the group consisting of SEQ ID NOs: 16-18; CDR2 sequences having an amino acid sequence of SEQ ID NO: 18; and CDR3 sequences consisting of an amino acid sequence selected from the group consisting of SEQ ID NOs: 20-22, respectively. Thus, such antibodies contain the $V_H$ and $V_L$ CDR sequences of monoclonal antibodies, yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. fol. Biol. 227:776-798; and Cox, J. P. L. et al., 1994 Eur. J Immunol. 24:827-836; the contents of each of which are expressly incorporated herein by reference.

An example of framework sequences for use in the antibodies of the invention are those that are structurally similar to the framework sequences used by selected antibodies of the invention, e.g., consensus sequences and/or framework sequences used by monoclonal antibodies of the invention. The $V_H$ CDR1, 2 and 3 sequences, and the $V_L$ CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180, 370 to Queen et al).

Another type of variable region modification is to mutate amino acid residues within the $V_H$ and/or $V_L$ CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) can be introduced. The mutations may be amino acid substitutions, additions or deletions. Moreover, typically no more than one, two, three, four or five residues within a CDR region are altered.

Accordingly, in another embodiment, the invention provides isolated anti-IL-13 monoclonal antibodies, or antigen binding portions thereof, consisting of a heavy chain variable region having: a $V_H$ CDR1 region consisting of an amino acid sequence selected from the group having SEQ ID NOs: 6-7 or an amino acid sequence having one, two, three, four or five amino acid substitutions, deletions or additions as compared to SEQ ID NOs: 6-7; a $V_H$ CDR2 region having an amino acid sequence of SEQ ID NO: 8, or an amino acid sequence having one, two, three, four or five amino acid substitutions, deletions or additions as compared to SEQ ID NO: 8; a $V_H$ CDR3 region having an amino acid sequence selected from the group consisting of SEQ ID NOs: 9-10, or an amino acid sequence having one, two, three, four or five amino acid substitutions, deletions or additions as compared to SEQ ID NOs: 9-10; a $V_L$ CDR1 region having an amino acid sequence selected from the group consisting of SEQ ID NOs: 16-18, or an amino acid sequence having one, two, three, four or five amino acid substitutions, deletions or additions as compared to SEQ ID NOs: 16-18; a $V_L$ CDR2 region having an amino acid sequence of SEQ ID NO: 19, or an amino acid sequence having one, two, three, four or five amino acid substitutions, deletions or additions as compared to SEQ ID NO: 19; and a $V_L$ CDR3 region having an amino acid sequence selected from the group consisting of SEQ ID NOs: 20-22, or an amino acid sequence having one, two, three, four or five amino acid substitutions, deletions or additions as compared to SEQ ID NOs: 20-22.

Engineered antibodies of the invention include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention.

Another type of framework modification involves mutating one or more residues within the framework region, or even within one or more CDR regions, to remove T cell—epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered Clq binding and/or reduced or abolished complement dependent cytotoxicity (CDC). This approach is described in further detail in U.S. Pat. No. 6,194,551 by Idusogie et at.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγR1, FcγRII, FcγRIII and FcRn have been mapped and variants with improved binding have been described (see Shields, R. L. et al., 2001 J. Biol. Chen. 276:6591-6604).

In still another embodiment, the glycosylation of an antibody is modified. For example, an aglycoslated antibody can be made (i.e., the antibody lacks glycosylation). Glycosylation can be altered to, for example, increase the affinity of the antibody for "antigen'. Such carbohydrate modifications can be accomplished by; for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1, 4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180). Another modification of the antibodies herein that is contemplated by the invention is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Methods of Engineering Antibodies

As discussed above, the anti-IL-13 antibodies having $V_H$ and $V_L$ sequences shown herein can be used to create new anti-IL-13 antibodies by modifying the $V_H$ and/or $V_L$ sequences, or the constant region(s) attached thereto. Thus, in another aspect of the invention, the structural features of an anti-IL-13 antibody of the invention are used to create structurally related anti-IL-13 antibodies that retain at least one functional property of the antibodies of the invention, such as binding to human IL-13 and also inhibiting one or more functional properties of IL-13 (e.g., receptor binding, inhibition of mediator release).

For example, one or more CDR regions of the antibodies of the present invention, or mutations thereof, can be combined recombinantly with known framework regions and/or other CDRs to create additional, recombinantly-engineered, anti-IL-13 antibodies of the invention, as discussed above. Other types of modifications include those described in the previous section. The starting material for the engineering method is one or more of the $V_H$ and/or $V_L$ sequences provided herein, or one or more CDR regions thereof. To create the engineered antibody, it is not necessary to actually prepare (i.e., express as a protein) an antibody having one or more of the $V_H$ and/or $V_L$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing an anti-IL-13 antibody consisting of: a heavy chain variable region antibody sequence having a CDR1 sequence selected from the group consisting of SEQ ID NOs: 6-7, a CDR2 sequence of SEQ ID NO: 8 and/or a CDR3 sequence selected from the group consisting of SEQ ID NOs: 9-10; and a light chain variable region antibody sequence having a CDR1 sequence selected from the group consisting of SEQ ID NOs: 16-18, a CDR2 sequence of SEQ ID NO: 19 and/or a CDR3 sequence selected from the group consisting of SEQ ID NOs: 20-22; altering at least one amino acid residue within the heavy chain variable region antibody sequence and/or the light chain variable region antibody sequence to create at least one altered antibody sequence; and expressing the altered antibody sequence as a protein.

Standard molecular biology techniques can be used to prepare and express the altered antibody sequence. The antibody encoded by the altered antibody sequence(s) is one that retains one, some or all of the functional properties of the anti-IL-13 antibodies described herein, which functional properties include, but are not limited to, specifically binding to human IL-13; and the antibody exhibits at least one of the following functional properties: the antibody inhibits binding of IL-13 protein to the IL-13 receptor, or the antibody inhibits IL-13 receptor binding preventing or ameliorating an inflammatory, fibrotic or allergic condition, particularly an inflammatory or obstructive airways disease, or the antibody inhibits IL-13 receptor binding thereby preventing or ameliorating asthma.

The altered antibody may exhibit one or more, two or more, or three or more of the functional properties discussed above.

The functional properties of the altered antibodies can be assessed using standard assays available in the art and/or described herein, such as those set forth in the Examples (e.g., ELISAs).

In certain embodiments of the methods of engineering antibodies of the invention, mutations can be introduced randomly or selectively along all or part of an anti-IL-13 antibody coding sequence and the resulting modified anti-IL-13 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of the Invention

Another aspect of the invention pertains to nucleic acid molecules that encode the antibodies of the invention. The nucleic acids may be present in whole cells, in a cell lysate, or may be nucleic acids in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. 1987 Current Protocols in Molecular Biology, Greene Publishing and Wiley Interscience, New York. A nucleic acid of the invention can be, for example, DNA or RNA and may or may not contain intronic sequences. In an embodiment, the nucleic acid is a cDNA molecule. The nucleic acid may be present in a vector such as a phage display vector, or in a recombinant plasmid vector.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from various phage clones that are members of the library.

Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to an scFv gene. In these manipulations, a $V_L$- or $V_H$-encoding DNA fragment is operatively linked to another DNA molecule, or to a fragment encoding another protein, such as an antibody constant region or a flexible linker. The term "operatively linked", as used in this context, is intended to mean that the two DNA fragments are joined in a functional manner, for example, such that the amino acid sequences encoded by the two DNA fragments remain in-frame, or such that the protein is expressed under control of a desired promoter.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g., Kabat, E. A., el al., 1991 Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as to a Fab light chain gene) by operatively linking the $V_L$-encoding DNA to another DNA molecule encoding the light chain constant region, CL. The sequences of human light chain constant region genes are known in the art (see e.g., Kabat, E. A., et al., 1991 Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or a lambda constant region.

To create an scFv gene, the $V_H$- and $V_L$-encoding DNA fragments are operatively linked to another fragment encoding a flexible linker, e.g., encoding the amino acid sequence (Gly4-Ser)$_3$, such that the $V_H$ and $V_L$ sequences can be expressed as a contiguous single-chain protein, with the $V_L$ and $V_H$ regions joined by the flexible linker (see e.g., Bird et al., 1988 Science 242:423-426; Huston et at., 1988 Proc. Natl. Acad. Sci. USA 85:5879-5883; McCafferty et al., 1990 Nature 348:552-554).

Production of Monoclonal Antibodies of the Invention

Monoclonal antibodies (mAbs) can be produced by a variety of techniques, including conventional monoclonal antibody methodology e.g., the standard somatic cell hybridization technique of Kohler and Milstein, 1975 Nature 256: 495. Many techniques for producing monoclonal antibody can be employed e.g., viral or oncogenic transformation of B lymphocytes.

An animal system for preparing hybridomas is the murine system. Hybridoma production in the mouse is a well established procedure Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693, 762 and, 6,180,370 to. Queen. et al.

In a certain embodiment, the antibodies of the invention are human monoclonal antibodies. Such human monoclonal antibodies directed against IL-13 can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy (μ and γ) and κ light chain immunoglobulin sequences, together with targeted mutations that inactivate the endogenous μ and κ chain loci (see e.g., Lonberg, et al., 1994 Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal (Lonberg, N. et al., 1994 supra; reviewed in Lonberg, N., 1994 Handbook of Experimental Pharmacology 113:49-101; Lonberg, N. and Huszar, D., 1995 Intern. Rev. Immunol. 13: 65-93, and Harding, F. and Lonberg, N., 1995 Ann. N. Y. Acad. Sci. 764:536-546). The preparation and use of HuMAb mice, and the genomic modifications carried by such mice, is further described in Taylor, L. et al., 1992 Nucleic Acids Research 20:6287-6295; Chen, J. et at., 1993 International Immunology 5: 647-656; Tuaillon et al., 1993 Proc. Natl. Acad. Sci. USA 94:3720-3724; Choi et al., 1993 Nature Genetics 4:117-123; Chen, J. et al., 1993 EMBO J. 12: 821-830; Tuaillon et al., 1994 J. Immunol. 152:2912-2920; Taylor, L. et al., 1994 International Immunology 579-591; and Fishwild, D. et al., 1996 Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92103918, WO 93/12227, WO 94/25585, WO 97113852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise anti-IL-13 antibodies of the invention. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-IL-13 antibodies of the invention. For example, mice carrying both a human heavy chain transchromosome and a human light chain tranchromosome, referred to as "TC mice" can be used; such mice are described in Tomizuka et al., 2000 Proc. Natl. Acad. Sci. USA 97:722-727. Furthermore, cows carrying human heavy and light chain transchromosomes have been described in the art (Kuroiwa et al., 2002 Nature Biotechnology 20:889-894) and can be used to raise anti-IL-13 antibodies of the invention.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Generation of Human Monoclonal Antibodies Against IL-13

Purified recombinant human (hr) IL-13 conjugated to Pan DR T helper Epitopes (PADRE), is used as the antigen. Fully human monoclonal antibodies to IL-13 are prepared using HCo7 strains of HuMab transgenic mice which express human antibody genes. In this mouse strain, the endogenous mouse kappa light chain gene can be homozygously disrupted as described in Chen et al., 1993 EMBO J. 12:811-820 and the endogenous mouse heavy chain gene can be homozygously disrupted as described in Example 1 of PCT Publication WO 01109187. This mouse strain carries a human kappa light chain transgene, KCo5, as described in Fishwild et al., 1996 Nature Biotechnology 14:845-851 and the HCo7 human heavy chain transgene as described in U.S. Pat. Nos. 5,545,806; 5,625,825; and 5,545,807.

To generate fully human monoclonal antibodies to IL-13 of the invention, HuMab mice are immunized with a mixture of purified recombinant IL-13 derived from HEK-EBNA/PADRE conjugate (42 ug/mouse) and Quil A (15 ug/mouse, Accurate Chemical). General immunization schemes for HuMab mice are described in Lonberg, N. et al., 1994 Nature 368(6474): 856-859; Fishwild, D. et al., 1996 Nature Biotechnology 14:845-851 and PCT Publication WO 98/24884. Transgenic mice are immunized either intravenously (IV), or subcutaneously (SC) between day 1-71. Mice are boosted intravenously with antigen (without adjuvant) 2 days before sacrifice and removal of the spleen. RNA was isolated from spleens using the Nucleospin RNA II isolation kit (BD Biosciences/Clontech). The RNA was used to generate a phage display library of randomly assorted H and L chain variable domains in a Fab phage display vector as described in U.S. Pat. No. 6,794,132. The phage display library was subjected to five rounds of selection using biotinylated hrIL-13 in a solution-phase equilibrium binding protocol as described in the patent. The first four rounds of selection employed hrIL-13 at $10^{-8}$ M and the last round of selection employed hrIL-13 at $10^{-9}$ M. The final signal to noise ratio determined by counting pfu's recovered in the presence of antigen divided by pfu's recovered in the absence of antigen was 37 for this library, indicating that greater than 90% of the phage selected were expressing antibodies that bound hrIL-13. The phage display library was then subcloned into a plasmid vector for the expression of soluble Fab as described in U.S. Pat. No. 6,794,132.

Generation of Transfectomas Producing Monoclonal Antibodies

Antibodies of the invention also can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the CH segment(s) within the vector and the $V_L$ segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. 1990). It will be appreciated by those skilled in the art that the design of the expression vector, including the selection of regulatory sequences, may depend on such factors as the choice of the host cell to be transformed, the level of expression of protein desired, etc. Regulatory sequences for mammalian host cell expression include viral elements that direct high levels of protein expression in mammalian cells, such as promoters and/or enhancers derived from cytomegalovirus (CMV), Simian Virus 40 (SV40), adenovirus (e.g., the adenovirus major late promoter (AdMLP)), and polyoma. Alternatively, nonviral regulatory sequences may be used, such as the ubiquitin promoter or P-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al., 1988 Mol. Cell. Biol. 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr– host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is theoretically possible to express the antibodies of the invention in either prokaryotic or eukaryotic host cells. Expression of antibodies in eukaryotic cells, in particular mammalian host cells, is discussed because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R., 1985 Immunology Today 6:12-13).

Mammalian host cells for expressing the recombinant antibodies of the invention include Chinese Hamster Ovary (CHO cells) (including dhfr-CHO cells, described Urlaub and Chasin, 1980 Proc. Natl. Acad. Sci. USA 77:4216-4220 used with a DH FR selectable marker, e.g., as described in R. J. Kaufman and P. A. Sharp, 1982 Mol. Biol. 159:601-621, NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods.

Immunoconjugates

In another aspect, the present invention features an anti-IL-13 antibody, or a fragment thereof, conjugated to a therapeutic moiety, such as a cytotoxin, a drug (e.g., an immunosuppressant) or a radiotoxin. Such conjugates are referred to herein as "immunoconjugates" Immunoconjugates that include one or more cytotoxins are referred to as "immunotoxins." A cytotoxin or cytotoxic agent includes any agent that is detrimental to (e.g., kills) cells. Examples include taxon, cytochalasin B, gramicidin D, ethidium bromide, emetine, mitomycin, etoposide, tenoposide, vincristine, vinblastine, t. colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), ablating agents (e.g., mechlorethamine, thioepa chloraxnbucil, meiphalan, carmustine (BSNU) and lomustine (CCNU), cyclothosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg™; Wyeth-Ayerst).

Cytotoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al., 2003 Adv. Drug Deliv. Rev. 55:199-215; Trail, P. A. et al., 2003 Cancer Immunol. Immunother. 52:328-337; Payne, G., 2003 Cancer Cell 3:207-212; Allen, T. M., 2002 Nat. Rev. Cancer 2:750-763; Pastan, I. and Kreitman, R. J., 2002 Curr. Opin. Investig. Drugs 3:1089-1091; Senter, P. D. and Springer, C. J., 2001 Adv. Drug Deliv. Rev. 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$, and lutetium$^{177}$. Method for preparing radioimmunconjugates are established in the art. Examples of radioimmunoconjugates are commercially available, including Zevalin™ (DEC Pharmaceuticals) and Bexxar™ (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et at., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Inmunol. Rev., 62:119-58 (1982).

Bispecific Molecules

In another aspect, the present invention features bispecific molecules comprising an anti-IL-13 antibody, or a fragment thereof, of the invention. An antibody of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for IL-13 and a second binding specificity for a second target epitope. For example, the second target epitope is an Fc receptor, e.g., human FcγR1(CD64) or a human Fcα receptor (CD89). Therefore, the invention includes bispecific molecules capable of binding both to FcγR, FcαR or FcεR expressing effector cells (e.g., monocytes, macrophages or polymorphonuclear cells (PMNs), and to target cells expressing IL-13. These bispecific molecules target IL-13 expressing cells to effector cell and trigger Fc receptor-mediated effector cell activities, such as phagocytosis of an IL-13 expressing cells, antibody dependent cell-mediated cytotoxicity (ADCC), cytokine release, or generation of superoxide anion.

Additionally, for the invention in which the bispecific molecule is multi-specific, the molecule can further include a third binding specificity, in addition to an anti-Fc binding specificity and an anti-IL-13 binding specificity. For example, the third binding specificity could be an anti-enhancement factor (EF) portion, e.g., a molecule which binds to a surface protein involved in cytotoxic activity and thereby increases the immune response against the target cell. The "anti-enhancement factor portion" could be an antibody, functional antibody fragment or a ligand that binds to a given molecule, e.g., an antigen or a receptor, and thereby results in an enhancement of the effect of the binding determinants for the Fc receptor or target cell antigen.

The "anti-enhancement factor portion" can bind an Fc receptor or a target cell antigen. Alternatively, the anti-enhancement factor portion could bind to an entity that is different from the entity to which the first and second binding specificities bind. For example, the anti-enhancement factor portion can bind a cytotoxic T-cell (e.g. by CD2, CD3, CD8, CD28, CD4, CD44, ICAM-1 or other immune cell that results in an increased immune response against the target cell).

In one embodiment, the bispecific molecules of the invention comprise as a binding specificity at least one antibody, or an antibody fragment thereof, including, e.g., an Fab, Fab', F(ab')₂, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three $F_\gamma$ receptor classes: FcγR1(CD64), FcγRII(CD32), and FcγRIII (CD 16). In another embodiment, the Fcγ receptor is a human high affinity FcγRI. The human FcγRI is a 72 kDa molecule, which shows high affinity for monomeric IgG ($10^8$-$10^9$ $M^{-1}$).

The production and characterization of certain anti-Fcγ monoclonal antibodies are described by Fanger et at. in PCT Publication WO 88/00052 and in U.S. Pat. No. 4,954,617, the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al., 1995 J. Immunol 155 (10): 4996-5002 and PCT Publication WO 94/10332. The 1122 antibody producing cell line was deposited at the American Type Culture Collection under the designation HA022CL1 and has the accession no. CRL 11177.

In still other embodiments, the binding specificity for an Fc receptor is provided by an antibody that binds to a human IgA receptor, e.g., an Fc-alpha receptor (FcαRI (CD89), the binding of which does not have to be blocked by human immunoglobulin A (IgA). The term "IgA receptor" is intended to include the gene product of one a gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity ($5 \times 10^7$ $M^{-1}$) for both IgA1 and IgA2, which is increased upon exposure to cytokines such as G-CSF or GM-CSF (Morton, H. C. et al., 1996 Critical Reviews in Immunology 116:423-440). Four FcαRI-specific monoclonal antibodies, identified as A3, A59, A62 and A77, which bind FcαRI outside the IgA ligand binding domain, have been described (Monteiro, R. C. et al., 1992 J. Immunol. 148:1764).

FcαRI and FcγRI are trigger receptors for use in the bispecific molecules of the invention because they are expressed primarily on immune effector cells, e.g., monocytes, PMNs, macrophages and dendritic cells; expressed at high levels (e.g., 5,000-100,000 per cell); mediators of cytotoxic activities (e.g., ADCC, phagocytosis); mediate enhanced antigen presentation of antigens, including self-antigens, targeted to them.

Other antibodies which can be employed in the bispecific molecules of the invention are murine, chimeric and humanized monoclonal antibodies.

The bispecific molecules of the present invention can be prepared by conjugating the constituent binding specificities, e.g., the anti-FcR and anti-IL-13 binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al., 1984 J. Exp. Med. 160:1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand x Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively 4 labeled and used in a radioimmunoassay (RIA) (see, for example, Weintraub; B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

Pharmaceutical Compositions

In another aspect, the present invention provides a composition, e.g., a pharmaceutical composition, containing one or a combination of monoclonal antibodies, or antigen-binding portion(s) thereof, of the present invention, formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

Pharmaceutical compositions of the invention also can be administered in combination therapy, i.e., combined with other agents. For example, the combination therapy can include an anti-IL-13 antibody of the present invention combined with at least one other anti-inflammatory agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g., by injection or infusion). Depending on the route of administration, the active compound, i.e., antibody, immunoconjuage, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al., 1977 J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and di-carboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as, aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, one can include isotonic agents, for example, sugars, polyalcohols such as mannitol, sorbitol, or sodium chloride in the composition. Prolonged absorption of the injectable compositions can be brought about by including in the composition an agent that delays absorption for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, from about 0.1 percent to about 70 percent, or from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Dosage regimens for an anti-IL-13 antibody of the invention may include 1 mg/kg body weight or 3 mg/kg body weight by intravenous or subcutaneous administration, with the antibody being given using one of the following dosing schedules: e.g. every four weeks for six dosages, then every three months; every three weeks; 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Alternatively, antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated or until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-IL-13 antibody of the invention can results in a decrease in severity of disease symptoms, an increase in frequency and duration of disease symptom-free periods, or a prevention of impairment or disability due to the disease affliction.

A composition of the present invention can be administered by one or more routes of administration using one or more of a variety of methods known in the art. As will be appreciated by the skilled artisan, the route and/or mode of administration will vary depending upon the desired results. Routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered by a nonparenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in one embodiment, a therapeutic composition of the invention can be administered with a needleless hypodermic injection device, such as the devices shown in U.S. Pat. Nos. 5,399,163; 5,383,851; 5,312,335; 5,064,413; 4,941,880; 4,790,824 or 4,596,556. Examples of well known implants and modules useful in the present invention include: U.S. Pat. No. 4,487,603, which shows an implantable micro-infusion pump for dispensing medication at a controlled rate; U.S. Pat. No. 4,486,194, which shows a therapeutic device for administering medicants through the skin; U.S. Pat. No. 4,447,233, which shows a medication infusion pump for delivering medication at a precise infusion rate; U.S. Pat. No. 4,447,224, which shows a variable flow implantable infusion apparatus for continuous drug delivery; U.S. Pat. No. 4,439,196, which shows an osmotic drug delivery system having multi-chamber compartments; and U.S. Pat. No. 4,475,196, which shows an osmotic drug delivery system. These patents are incorporated herein by reference. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade, 1989 J. Cline Pharmacol. 29:685). Exemplary targeting moieties include folate or biotin (see, e.g., U.S. Pat. No. 5,416,016 to Low et al.); mannosides (Umezawa et al., 1988 Biochem. Biophys. Res. Commun 153:1038); antibodies (P. G. Bloeman et al., 1995 FEBS Lett. 357:140; M. Owais et al., 1995 Antimicrob. Agents Chernother. 39:180); surfactant protein A receptor (Briscoe et al., 1995 Am. J. Physiol. 1233:134); p120 (Schreier et al., 1994 J. Biol. Chem. 269:9090); see also K. Keinanen; M. L. Laukkanen, 1994 FEBSLett. 346:123; J. J. Killion; I. J. Fidler, 1994 Imrnunomethods 4:273.

Uses and Methods of the Invention

The antibodies (and immunoconjugates and bispecific molecules) of the present invention have in vitro and in vivo diagnostic and therapeutic utilities. For example, these molecules can be administered to cells in culture, e.g. in vitro or in vivo, or in a subject, e.g., in vivo, to treat, prevent or diagnose a variety of disorders. The term "subject" as used herein in intended to include human and non-human animals. Non-human animals includes all vertebrates, e.g., mammals and non-mammals, such as non-human primates, sheep, dogs, cats, cows, horses, chickens, amphibians, and reptiles. The methods are particularly suitable for treating human patients having a disorder associated with aberrant IL-13 expression. When antibodies to IL-13 are administered together with another agent, the two can be administered in either order or simultaneously.

In one embodiment, the antibodies (and immunoconjugates and bispecific molecules) of the invention can be used to detect levels of IL-13, or levels of cells that contain IL-13. This can be achieved, for example, by contacting a sample (such as an in vitro sample) and a control sample with the anti-IL-13 antibody under conditions that allow for the formation of a complex between the antibody and IL-13. Any complexes formed between the antibody and IL-13 are detected and compared in the sample and the control. For example, standard detection methods, well known in the art, such as ELISA and flow cytometic assays, can be performed using the compositions of the invention.

Accordingly, in one aspect, the invention further provides methods for detecting the presence of IL-13 (e.g., human IL-13 antigen) in a sample, or measuring the amount of IL-13, comprising contacting the sample, and a control sample, with an antibody of the invention, or an antigen binding portion thereof, which specifically binds to IL-13, under conditions that allow for formation of a complex between the antibody or portion thereof and IL-13. The formation of a complex is then detected, wherein a difference in complex formation between the sample compared to the control sample is indicative of the presence of IL-13 in the sample.

Also within the scope of the invention are kits consisting of the compositions (e.g., antibodies, human antibodies, immunoconjugates and bispecific molecules) of the invention and instructions for use. The kit can further contain a least one additional reagent, or one or more additional antibodies of the invention (e.g., an antibody having a complementary activity which binds to an epitope on the target antigen distinct from the first antibody). Kits typically include a label indicating the intended use of the contents of the kit. The term label includes any writing, or recorded material supplied on or with the kit, or which otherwise accompanies the kit.

The invention having been fully described, it is further illustrated by the following examples and claims, which are illustrative and are not meant to be further limiting. Those skilled in the art will recognize or be able to ascertain using no more than routine experimentation, numerous equivalents to the specific procedures described herein. Such equivalents are within the scope of the present invention and claims. The contents of all references, including issued patents and published patent applications, cited throughout this application are hereby incorporated by reference.

EXAMPLES

Example 1

Generation of Human IL-13-Specific Antibodies from Immunized Splenic Libraries

The RNA from spleen was used to generate a phage display library of randomly assorted H and L chain variable domains in a Fab phage display vector as described in U.S. Pat. No. 6,794,132. The phage display library was subjected to five rounds of selection using biotinylated hrIL-13 in a solution-phase equilibrium binding protocol as described in the patent. The first four rounds of selection employed hrIL-13 at $10^{-8}$ M and the last round of selection employed hrIL-13 at $10^{-9}$ M. The final signal to noise ratio determined by counting pfu's recovered in the presence of antigen divided by pfu's recovered in the absence of antigen was 37 for this library, indicating that greater than 90% of the phage selected were expressing antibodies that bound hrIL-13. The phage display library was then subcloned into a plasmid vector for the expression of soluble Fab as described in U.S. Pat. No. 6,794,132. The subcloned is library comprises plasmid vectors in E. coli, each plasmid encoding a monoclonal Fab fragment. The subclone library was plated out and colonies representing individual clones were picked to inoculate 96-well plates. After overnight growth, the plate cultures were used to archive frozen cell banks for the clones in 96-well plates and also to seed replica 96-well plates which were induced to express monoclonal antibodies. The next day, these 96-well plate cultures were subjected to detergent extraction and purification to recover microgram quantities of antibodies. The purified antibodies were treated to remove endotoxin and sterile filtered terminally. ELISA assays were conducted using biotinylated rhIL-13 coated on avidin plates to identify which wells contained functional positives. Sandwich assays targeting the constant region of the antibodies were used to determine antibody concentrations in different wells. The 96-well plates containing the antibodies and the assay data were assessed for biological activity. The clones of interest in the 96-well frozen cell banks were then sequenced to identify the ones expressing unique antibodies. Subsequently, the frozen cell banks of these unique clones were used to seed small scale shake flask cultures and grown overnight. Large scale flasks were seeded using the overnight cultures and then induced to express antibodies. The next day, the flask cultures were mechanically homogenized and purified to yield milligram quantities of antibodies. The purified Fabs were processed for endotoxin removal and subjected to terminal sterile filtration. The functional activity of these antibodies was demonstrated by ELISA using biotinylated rhIL-13 coated on avidin plates. The antibody concentrations were determined by absorbance measurement at 280 nm. The purified Fabs were assessed for in vitro binding and activity in a cell based assay.

Example 2

Quantitative Analysis of Binding Affinities: Determination of Anti-Human IL-13 Fab Candidates Surface plasmon resonance measurements quantifying the interaction of anti-IL-13 Fabs with several hrIL-13 are performed using the optical biosensor, BIAcore 2000. Specific binding of IL-13 to a respective IL-13 Fab immobilized on a BIAcore chip can be measured by following accumulation of the ligand on the receptor. The microscopic association ($k_{on}$) and dissociation rates ($k_{off}$) can be obtained directly from the mass accumulation rates on the chip and are expressed in response units (RUs). Anti-IL-13 Fab is immobilized on the chip surface via a secondary anti-human LK antibody (Jackson Immunochemicals). This capture antibody was covalently bound using the 'Amine coupling kit' (BIAcore, Cat. No. BR-1000-50) as recommended in the manufacturers' protocols. 250 µl of varying concentrations of hrIL-13 was injected at flow rate of 20 µl/min and the kinetic trace was recorded. The chip surface was regenerated by two acid wash steps using 100 mM HCl and injecting 10

μl with a flow rate of 20 μl/min. This treatment leads to dissociation of the Fab IL-13 complex due to reversible acid denaturation. No significant loss of binding activity was observed when the antibody was reinjected for a subsequent run. The kinetic traces were evaluated with the BIAcore software applying the 1:1 Langmuir association model The summarized affinity data on human IL-13 is shown in Table 1 herein.

TABLE 1

| Fab | KD [pM] human IL-13 |
|---|---|
| 01471/G6 | 100 ± 2 |
| 03161/H2 | 197 ± 12 |
| 01951/G12 | 480 ± 68 |
| 01771/E10 | 343 ± 54 |

Example 3

Conversion into the IgG Format

Antibody DNA sequencing templates were purified from 3 ml cultures using QIAprep minipreps (Qiagen Inc.). Templates were sequenced using an Applied Biosystems 3100 Avant Genetic Analyzer according to manufacturer's specifications. The heavy and kappa chain variable regions of selected clones were separately amplified from the sequencing templates by PCR, purified by agarose gel electrophoresis, and excised and purified from the gel. Plasmids encoding the $V_H$ and $V_L$ were cloned into expression cassettes for human kappa light and human IgG$_1$ heavy chains. The Sp2/0 parental cell line was transfected with two vectors, one for the light and one for heavy chain vectors. Transfected cells were selected and amplified using G418 and methotrexate respectively resulting in the emergence of resistant, amplified cell pools producing the antibodies with titers ranging from 5 mg/L to 30 mg/L. Dilution cloning was then employed, resulting in the isolation of 127 viable clones from six 96-well plates. Emerging cell lines were then tested for productivity in a fed-batch shaker format. Stability testing to confirm the stable integration of the expression constructs and robust expression of product were also performed over a 90-day period. Northern blots exhibited single, full length RNAs with equal band intensities, indicating similar expression levels for both the heavy chain and light chain.

Example 4

In Vitro Characterization of Anti-IL-13 Full Antibodies in a Cell Based Assay

IL-13 is a potent inducer of eotaxin release from human lung fibroblasts. The ability of the antibodies to neutralize the bioactivity of IL-13 was assessed in an IL-13-induced eotaxin release assay using human lung fibroblasts. Briefly, cells ($2\times10^4$ cells per well in a volume of 100 μl) were plated out in each well of a 96 well tissue culture plate. The cells were stimulated with a concentration of IL-13 conferring 80% of the maximal eotaxin release, which was pre-determined for each batch of cells using a standard curve of 0-100 ng/ml IL-13. Varying concentrations of the antibodies were co-applied to the cells. The cells were allowed to incubate for 24 h at 37° C., 5% $CO_2$ and the culture media was harvested and stored at −20° C. until required. Eotaxin levels within the media were measured by specific ELISA (R&D systems) where the sensitivity of assay was between 15-1000 pg/ml.

The anti-IL-13 Fabs were thereby analyzed with respect to $EC_{50}$ as described above and shown in Table 2.

TABLE 2

| Antibody | $EC_{50}$ [nM] human IL-13 |
|---|---|
| 01471/G6 | 1.23 ± 0.4 |
| 03161/H2 | 0.95 ± 0.2 |
| 01951/G12 | 0.33 ± 0.1 |
| 01771/E10 | 1.71 ± 0.5 |

Example 5

Sequence Analysis of the Anti-IL-13 Antibodies

The nucleotide sequences of the heavy and light chain variable regions ($V_H$ and $V_L$) of all antibodies were determined Amino acid sequences of the complementarity determining regions (CDRs) are listed in Table 3 and 4 herein. The CDRs according Kabat definition (E. Kabat et al, 1991, Sequences of Proteins of Immunological Interest, 5th edition, Public Health Service, National Institute of Health, Bethesda, Md., are listed in Table 3a and 4a.

TABLE 3

| Antibody | HCDR1 | SEQ ID No. HCDR1 | HCDR2 | SEQ ID No. HCDR2 | HCDR3 | SEQ ID No. HCDR3 |
|---|---|---|---|---|---|---|
| 01471/G6 | GFTFSNYG | 1 | IWYDGSN | 3 | VKGSGDIP | 4 |
| 03161/H2 | GFTFSNYG | 1 | IWYDGSN | 3 | VKGSGDIP | 4 |
| 01951/G12 | GFTFSSYG | 2 | IWYDGSN | 3 | ARLWFGDLD | 5 |
| 01771/E10 | GFTFSSYG | 2 | IWYDGSN | 3 | ARLWFGDLD | 5 |

TABLE 3a

| Antibody | HCDR1 | SEQ ID No. HCDR1 | HCDR2 | SEQ ID No. HCDR2 | HCDR3 | SEQ ID No. HCDR3 |
|---|---|---|---|---|---|---|
| 01471/G6 | NYGMH | 6 | IIWYDGSNKYYADSVKG | 8 | GSGDIPFDY | 9 |
| 03161/H2 | NYGMH | 6 | IIWYDGSNKYYADSVKG | 8 | GSGDIPFDY | 9 |
| 01951/G12 | SYGMH | 7 | IIWYDGSNKYYADSVKG | 8 | LWFGDLDAFDI | 10 |
| 01771/E10 | SYGMH | 7 | IIWYDGSNKYYADSVKG | 8 | LWFGDLDAFDI | 10 |

TABLE 4

| Antibody | LCDR1 | SEQ ID No. LCDR1 | LCDR2 | SEQ ID No. LCDR2 | LCDR3 | SEQ ID No. LCDR3 |
|---|---|---|---|---|---|---|
| 01471/G6 | QSVSSY | 11 | DA | 12 | HQRSHWPPI | 13 |

TABLE 4-continued

| Antibody | LCDR1 | SEQ ID No. LCDR1 | LCDR2 | SEQ ID No. LCDR2 | LCDR3 | SEQ ID No. LCDR3 |
|---|---|---|---|---|---|---|
| 03161/H2 | QSVSSY | 11 | DA | 12 | HQRSHWPPI | 13 |
| 01951/G12 | QSVSSY | 11 | DA | 12 | QQRSSWPPV | 14 |
| 01771/E10 | QSVSSY | 11 | DA | 12 | HQRSSWPPI | 15 |

TABLE 4a

| Antibody | LCDR1 | SEQ ID No. LCDR1 | LCDR2 | SEQ ID No. LCDR2 | LCDR3 | SEQ ID No. LCDR3 |
|---|---|---|---|---|---|---|
| 01471/G6 | RASQSVSSYLA | 16 | DASNRAT | 19 | HQRSHWPPIFT | 20 |

TABLE 4a-continued

| Antibody | LCDR1 | SEQ ID No. LCDR1 | LCDR2 | SEQ ID No. LCDR2 | LCDR3 | SEQ ID No. LCDR3 |
|---|---|---|---|---|---|---|
| 03161/H2 | RASQSVSSYLA | 16 | DASNRAT | 19 | HQRSHWPPIFT | 20 |
| 01951/G12 | RAGQSVSSYLV | 17 | DASNRAT | 19 | QQRSSWPPVYT | 21 |
| 01771/E10 | RASQSVSSYLA | 18 | DASNRAT | 19 | HQRSSWPPIFT | 22 |

The sequences of the antibodies of the previous tables, including framework regions, are shown below. The full IgG1 antibody light and heavy chain constant regions are also shown below, incorporating, as an example, the variable regions of antibody 01951/G12 (emboldened).

01471/G6 Antibody Sequence (i) HC Variable Region

The HC variable amino acid sequence for 01471/G6 is shown in SEQ ID NO: 23 and is encoded by the nucleotide sequence shown in SEQ ID NO: 24

```
 E   V   Q   L   V   E   S   G   G   G   V   V   Q   P   G   R   S   L   R   L
gaagtgcagctggtggagtctgggggaggcgtggtccagcctgggaggtccctgagactc    60

S   C   A   A   S   G   F   T   F   S   N   Y   G   M   H   W   V   R   Q   A
tcctgtgcagcgtctggattcaccttcagtaactatggcatgcactgggtccgccaggct   120

P   G   K   G   L   E   W   V   A   I   I   W   Y   D   G   S   N   K   Y   Y
ccaggcaaggggctggagtgggtggcaattatatggtatgatggaagtaataaatactat   180

A   D   S   V   K   G   R   F   T   I   S   R   D   N   S   K   N   T   L   Y
gcagactccgtgaagggccgattcaccatctccagagacaattccaagaacacgctgtat   240

L   Q   M   N   S   L   R   A   E   D   T   A   V   Y   Y   C   V   K   G   S
ctgcaaatgaacagtctgagagccgaggacacggctgtgtattactgtgtgaaaggatct   300

G   D   I   P   F   D   Y   W   G   Q   G   T   L   V   T     (SEQ ID NO: 23)
ggggatattccctttgactactggggccagggaaccctggtcacc   345 (SEQ ID NO: 24)
```

(ii) LC Variable Region

The LC variable amino acid sequence for 01471/G6 is shown in SEQ ID NO: 25 and is encoded by the nucleotide sequence shown in SEQ ID NO: 26

```
 E   I   V   L   T   Q   S   P   A   T   L   S   S   S   P   G   E   R   A   T
gaaattgtgttgacgcagtctccagccaccctgtcttcgtctccaggggaaagagccacc    60

L   S   C   R   A   S   Q   S   V   S   S   Y   L   A   W   Y   Q   Q   K   P
ctctcctgcagggccagtcagagtgttagcagctacttagcctggtaccaacagaaacct   120

G   Q   A   P   R   L   L   I   Y   D   A   S   N   R   A   T   G   I   P   A
ggccaggctcccaggctcctcatctatgatgcatccaacagggccactggcatcccagcc   180

R   F   S   G   S   G   S   G   T   D   F   T   L   T   I   S   S   L   E   P
aggttcagtggcagtgggtctgggacagacttcactctcaccatcagcagcctagagcct   240

E   D   F   A   V   Y   Y   C   H   Q   R   S   H   W   P   P   I   F   T   F
gaagattttgcagtctattactgtcatcagcgtagccactggcctcccatattcactttc   300

G   P   G   T     (SEQ ID NO: 25)
ggccctgggacc   312 (SEQ ID NO: 26)
```

03161/H2 Antibody
(i) HC Variable Region
The HC variable amino acid sequence for 03161/H2 is shown in SEQ ID NO: 27 and is encoded by the nucleotide sequence shown in SEQ ID NO: SEQ ID No. 28

```
E  V  Q  L  V  E  S  G  G  G  V  V  Q  P  G  R  S  L  R  L
gaagtgcagctggtggagtctgggggaggcgtggtccagcctggaggtccctgagactc     60

S  C  A  A  S  G  F  T  F  S  N  Y  G  M  H  W  V  R  Q  A
tcctgtgcagcgtctggattcaccttcagtaactatggcatgcactgggtccgccaggct  120

P  G  K  G  L  E  W  V  A  I  I  W  Y  D  G  S  N  K  Y  Y
ccaggcaagggctggagtgggtggcaattatatggtatgatggaagtaataaatactat   180

A  D  S  V  K  G  R  F  T  I  S  R  D  N  S  K  N  T  L  Y
gcagactccgtgaagggccgattcaccatctccagagacaattccaagaacacgctgtat  240

L  Q  M  N  S  L  R  A  E  D  T  A  V  Y  Y  C  V  K  G  S
ctgcaaatgaacagtctgagagccgaggacacggctgtgtattactgtgtgaaaggatct  300

G  D  I  P  F  D  Y  W  G  Q  G  T  L  V  T        (SEQ ID NO: 27)
ggggatattccctttgactactggggccagggaaccctggtcacc    345>  (SEQ ID NO: 28)
```

(ii) LC Variable Region
The LC variable amino acid sequence for 03161/H2 is shown in SEQ ID NO: 29 and is encoded by the nucleotide sequence shown in SEQ ID NO: 30

```
E  I  V  L  T  Q  S  P  A  T  L  S  S  S  P  G  E  R  A  T
gaaattgtgttgacgcagtccccagccaccctgtcttcgtctccaggggaaagagccacc   60

L  S  C  R  A  S  Q  S  V  S  S  Y  L  A  W  Y  Q  Q  K  P
ctctcctgcagggccagtcagagtgttagcagctacttagcctggtaccaacagaaacct  120

G  Q  A  P  R  L  L  I  Y  D  A  S  N  R  A  T  G  T  P  A
ggccaggctcccaggctcctcatctatgatgcatccaacagggccactggcaccccagcc  180

R  F  S  G  S  G  S  G  T  D  F  T  L  T  I  S  S  L  E  P
aggttcagtggcagtgggtctgggacagacttcactctcaccatcagcagcctagagcct  240

E  D  F  A  V  Y  Y  C  H  Q  R  S  H  W  P  P  I  F  T  F
gaagattttgcagtctattactgtcatcagcgtagccactggcctcccatattcactttc  300

G  P  G  T        (SEQ ID NO: 29)
ggccctgggacc  312  (SEQ ID NO: 30)
```

01951/G12 Antibody Sequence
(i) HC Variable Region
The HC variable amino acid sequence for 01951/G12 is shown in SEQ ID NO: 31 and is encoded by the nucleotide sequence shown in SEQ ID NO: 32

```
E  V  Q  L  V  E  S  G  G  G  V  V  Q  P  G  R  S  L  R  L
gaagtgcagctggtggtgtctgggggaggcgtggtccagcctggaggtccctgagactc    60

S  C  A  A  S  G  F  T  F  S  S  Y  G  M  H  W  V  R  Q  A
tcctgtgcagcgtctggattcaccttcagtagctatggcatgcactgggtccgccaggct  120

P  G  K  G  L  E  W  V  A  I  I  W  Y  D  G  S  N  K  Y  Y
ccaggcaagggctggagtgggtggcaattatatggtatgatggaagtaataaatactat   180

A  D  S  V  K  G  R  F  T  I  S  R  D  N  S  K  N  T  L  Y
gcggactccgtgaagggccgattcaccatctccagagacaattccaagaacacgctgtat  240

L  Q  M  N  S  L  R  A  E  D  T  A  V  Y  Y  C  A  R  L  W
ctgcaaatgaacagcctgagagccgaggacacggctgtgtattactgtgcgaggctatgg  300

F  G  D  L  D  A  F  D  I  W  G  Q  G  T  M  V  T        (SEQ ID NO: 31)
ttcggggacttagatgcttttgatatctggggccaagggacaatggtcacc  351 (SEQ ID NO: 32)
```

(ii) LC Variable Region
The LC variable amino acid sequence for 01951/G12 is shown in SEQ ID NO: 33 and is encoded by the nucleotide sequence shown in SEQ ID NO: 34

```
E   I   V   L   T   Q   S   P   A   T   L   S   L   S   P   G   E   R   A   I
gaaattgtgttgacgcagtctccagccaccctgtctttgtctccaggggaaagagccatc      60

L   S   C   R   A   G   Q   S   V   S   S   Y   L   V   W   Y   Q   Q   K   P
ctctcctgcagggccggtcagagtgttagcagttacttagtctggtaccaacagaaacct    120

G   Q   A   P   R   L   L   I   Y   D   A   S   N   R   A   T   G   I   P   A
ggccaggctcccaggctcctcatctatgatgcatccaacagggccactggcatcccagcc    180

R   F   S   G   S   G   S   G   T   D   F   T   L   T   I   S   S   L   E   P
aggttcagtggcagtgggtctgggacagacttcactctcaccatcagcagcctagagcct    240

E   D   F   A   V   Y   Y   C   Q   Q   R   S   S   W   P   P   V   Y   T   F
gaagattttgcagtttattactgtcagcagcgcagcagctggcctccggtgtacactttt    300

G   Q   G   T           (SEQ ID NO: 33)
ggccaggggacc   312  (SEQ ID NO: 34)
```

01771/E10 Antibody Sequence
(i) HC Variable Region
The HC variable amino acid sequence for 01771/E10 is shown in SEQ ID NO: 35 and is encoded by the nucleotide sequence shown in SEQ ID NO: 36

```
Q   V   Q   L   V   Q   S   G   G   G   V   V   Q   P   G   R   S   L   R   L
caggtgcagctggtgcagtctgggggaggcgtggtccagcctgggaggtccctgagactc     60

S   C   A   A   S   G   F   T   F   S   S   Y   G   M   H   W   V   R   Q   A
tcctgtgcggcgtctggattcaccttcagtagctatggcatgcactgggtccgccaggct    120

P   G   K   G   L   E   W   V   A   I   I   W   Y   D   G   S   N   K   Y   Y
ccaggcaaggggctggagtgggtggcaattatatggtatgatggaagtaataaatactat    180

A   D   S   V   K   G   R   F   T   I   S   R   D   N   S   K   N   T   L   Y
gcggactccgtgaagggccgattcaccatctccagagacaattccaagaacacgctatat    240

L   Q   M   N   S   L   R   A   E   D   T   A   V   Y   Y   C   A   R   L   W
ctacaaatgaacagcctgagagccgaggacacggctgtgtattactgtgcgaggctatgg    300

F   G   D   L   D   A   F   D   I   W   G   Q   G   T   M   V   T       (SEQ ID NO: 35)
ttcggggacttagatgcttttgatatctggggccaagggacaatggtcacc    351  (SEQ ID NO: 36)
```

(ii) LC Variable Region
The LC variable amino acid sequence for 01771/E10 is shown in SEQ ID NO: 37 and is encoded by the nucleotide sequence shown in SEQ ID NO: 38

```
E   I   V   L   T   Q   S   P   A   T   L   S   L   S   P   G   E   R   A   T
gaaattgtgttgacgcagtctccagccaccctgtctttgtctccaggggaaagagccacc     60

L   S   C   R   A   S   Q   S   V   S   S   Y   L   A   W   Y   Q   Q   K   P
ctctcctgcagggccagtcagagtgttagcagctacttagcctggtaccaacagaaacct    120

G   Q   A   P   R   L   L   I   Y   D   A   S   N   R   A   T   G   I   P   A
ggccaggctcccaggctcctcatctatgatgcatccaacagggccactggcatcccagcc    180

R   F   S   G   S   G   S   G   T   D   F   T   L   T   I   S   S   L   E   P
aggttcagtggcagtgggtctgggacagacttcactctcaccatcagcagcctagagcct    240

E   D   F   A   V   Y   Y   C   H   Q   R   S   S   W   P   P   I   F   T   F
gaagattttgcggtttattactgtcatcagcgtagcagctggccccccgatattcactttc    300

G   P   G   T           (SEQ ID NO: 37)
ggccctgggacc   312  (SEQ ID NO: 38)
```

Full Antibody IgG1 Light Chain Sequence Incorporating the Variable Region of Antibody 01951/G12 (Emboldened)
The LC amino acid sequence is shown in SEQ ID NO: 39 and is encoded by the nucleotide sequence of SEQ ID NO: 40

```
         M   S   V   L   T   Q   V   L   A   L   L   L   W   L   T   G
   1     ATGAGTGTGC TCACTCAGGT CCTGGCGTTG CTGCTGCTGT GGCTTACAGG

T   R   C   E   I   V   L   T   Q   S   P   A   T   L   S   L   S
  51     TACGCGTTGT GAAATTGTGT TGACGCAGTC TCCAGCCACC CTGTCTTTGT

P   G   E   R   A   I   L   S   C   R   A   G   Q   S   V   S
 101     CTCCAGGGGA AAGAGCCATC CTCTCCTGCA GGGCCGGTCA GAGTGTTAGC

S   Y   L   V   W   Y   Q   Q   K   P   G   Q   A   P   R   L   L
 151     AGTTACTTAG TCTGGTACCA ACAGAAACCT GGCCAGGCTC CCAGGCTCCT

I   Y   D   A   S   N   R   A   T   G   I   P   A   R   F   S   G
 201     CATCTATGAT GCATCCAACA GGGCCACTGG CATCCCAGCC AGGTTCAGTG

S   G   S   G   T   D   F   T   L   T   I   S   S   L   E   P
 251     GCAGTGGGTC TGGGACAGAC TTCACTCTCA CCATCAGCAG CCTAGAGCCT

E   D   F   A   V   Y   Y   C   Q   Q   R   S   S   W   P   P   V
 301     GAAGATTTTG CAGTTTATTA CTGTCAGCAG CGCAGCAGCT GGCCTCCGGT

Y   T   F   G   Q   G   T   K   L   E   I   K   R   T   V   A   A
 351     GTACACTTTT GGCCAGGGGA CCAAGCTTGA AATCAAACGA ACTGTGGCTG

P   S   V   F   I   F   P   P   S   D   E   Q   L   K   S   G
 401     CACCATCTGT CTTCATCTTC CCGCCATCTG ATGAGCAGTT GAAATCTGGA

T   A   S   V   V   C   L   L   N   N   F   Y   P   R   E   A   K
 451     ACTGCCTCTG TTGTGTGCCT GCTGAATAAC TTCTATCCCA GAGAGGCCAA

V   Q   W   K   V   D   N   A   L   Q   S   G   N   S   Q   E   S
 501     AGTACAGTGG AAGGTGGATA ACGCCCTCCA ATCGGGTAAC TCCCAGGAGA

V   T   E   Q   D   S   K   D   S   T   Y   S   L   S   S   T
 551     GTGTCACAGA GCAGGACAGC AAGGACAGCA CCTACAGCCT CAGCAGCACC

L   T   L   S   K   A   D   Y   E   K   H   K   V   Y   A   C   E
 601     CTGACGCTGA GCAAAGCAGA CTACGAGAAA CACAAAGTCT ACGCCTGCGA

V   T   H   Q   G   L   S   S   P   V   T   K   S   F   N   R   G
 651     AGTCACCCAT CAGGGCCTGA GCTCGCCCGT CACAAAGAGC TTCAACAGGG

E   C   *      (SEQ ID NO: 39)
 701     GAGAGTGTTA G  (SEQ ID NO: 40)
```

Full Antibody IgG1 Heavy Chain Sequence Incorporating the Variable Region of Antibody 01951/G12 (Emboldened)
The HC amino acid sequence is shown in SEQ ID NO: 41 and is encoded by the nucleotide sequence of SEQ ID NO: 42

```
         M   A   W   V   W   T   L   P   F   L   M   A   A   A   Q   S   V
   1     ATGGCTTGGG TGTGGACCTT GCCATTCCTG ATGGCAGCTG CCCAAAGTGT

Q   A   E   V   Q   L   V   E   S   G   G   V   V   Q   P   G
  51     CCAGGCAGAA GTGCAGCTGG TGGAGTCTGG GGGAGGCGTG GTCCAGCCTG

R   S   L   R   L   S   C   A   A   S   G   F   T   F   S   S
 101     GGAGGTCCCT GAGACTCTCC TGTGCAGCGT CTGGATTCAC CTTCAGTAGC

Y   G   M   H   W   V   R   Q   A   P   G   K   G   L   E   W   V
 151     TATGGCATGC ACTGGGTCCG CCAGGCTCCA GGCAAGGGGC TGGAGTGGGT

A   I   I   W   Y   D   G   S   N   K   Y   Y   A   D   S   V   K
 201     GGCAATTATA TGGTATGATG GAAGTAATAA ATACTATGCG GACTCCGTGA

G   R   F   T   I   S   R   D   N   S   K   N   T   L   Y   L
 251     AGGGCCGATT CACCATCTCC AGAGACAATT CCAAGAACAC GCTGTATCTG
```

-continued

```
         Q   M   N   S       L   R   A       E   D   T       A   V   Y   Y       C   A   R
 301   CAAATGAACA   GCCTGAGAGC   CGAGGACACG   GCTGTGTATT   ACTGTGCGAG

L   W   F       G   D   L   D       A   F   D       I   W       G   Q   G   T   M
 351   GCTATGGTTC   GGGGACTTAG   ATGCTTTTGA   TATCTGGGGC   CAAGGGACAA

V   T   V       S   S   A       S   T   K   G       P   S   V       F   P   L
 401   TGGTCACCGT   CTCCTCAGCC   TCCACCAAGG   GCCCATCGGT   CTTCCCCCTG

A   P   S   S       K   S   T       S   G   G       T   A   A   L       G   C   L
 451   GCACCCTCCT   CCAAGAGCAC   CTCTGGGGGC   ACAGCGGCCC   TGGGCTGCCT

V   K   D       Y   F   P   E       P   V   T       V   S   W       N   S   G   A
 501   GGTCAAGGAC   TACTTCCCCG   AACCGGTGAC   GGTGTCGTGG   AACTCAGGCG

L   T   S       G   V   H       T   F   P   A       V   L   Q       S   S   G
 551   CCCTGACCAG   CGGCGTGCAC   ACCTTCCCGG   CTGTCCTACA   GTCCTCAGGA

L   Y   S   L       S   S   V       V   T   V       P   S   S   S       L   G   T
 601   CTCTACTCCC   TCAGCAGCGT   CGTGACCGTG   CCCTCCAGCA   GCTTGGGCAC

Q   T   Y       I   C   N   V       N   H   K       P   S   N       T   K   V   D
 651   CCAGACCTAC   ATCTGCAACG   TGAATCACAA   GCCCAGCAAC   ACCAAGGTGG

K   R   V       E   P   K       S   C   D   K       T   H   T       C   P   P
 701   ACAAGAGAGT   TGAGCCCAAA   TCTTGTGACA   AAACTCACAC   ATGCCCACCG

C   P   A   P       E   L   L       G   G   P       S   V   F   L       F   P   P
 751   TGCCCAGCAC   CTGAACTCCT   GGGGGGACCG   TCAGTCTTCC   TCTTCCCCCC

K   P   K       D   T   L   M       I   S   R       T   P   E       V   T   C   V
 801   AAAACCCAAG   GACACCCTCA   TGATCTCCCG   GACCCCTGAG   GTCACATGCG

V   V   D       V   S   H       E   D   P   E       V   K   F       N   W   Y
 851   TGGTGGTGGA   CGTGAGCCAC   GAAGACCCTG   AGGTCAAGTT   CAACTGGTAC

V   D   G   V       E   V   H       N   A   K       T   K   P   R       E   E   Q
 901   GTGGACGGCG   TGGAGGTGCA   TAATGCCAAG   ACAAAGCCGC   GGGAGGAGCA

Y   N   S       T   Y   R   V       V   S   V       L   T   V       L   H   Q   D
 951   GTACAACAGC   ACGTACCGTG   TGGTCAGCGT   CCTCACCGTC   CTGCACCAGG

W   L   N       G   K   E       Y   K   C   K       V   S   N       K   A   L
1001   ACTGGCTGAA   TGGCAAGGAG   TACAAGTGCA   AGGTCTCCAA   CAAAGCCCTC

P   A   P   I       E   K   T       I   S   K       A   K   G   Q       P   R   E
1051   CCAGCCCCCA   TCGAGAAAAC   CATCTCCAAA   GCCAAAGGGC   AGCCCCGAGA

P   Q   V       Y   T   L   P       P   S   R       E   E   M       T   K   N   Q
1101   ACCACAGGTG   TACACCCTGC   CCCCATCCCG   GGAGGAGATG   ACCAAGAACC

V   S   L       T   C   L       V   K   G   F       Y   P   S       D   I   A
1151   AGGTCAGCCT   GACCTGCCTG   GTCAAAGGCT   TCTATCCCAG   CGACATCGCC

V   E   W       E   S   N   G       Q   P   E       N   N   Y   K       T   T   P
1201   GTGGAGTGGG   AGAGCAATGG   GCAGCCGGAG   AACAACTACA   AGACCACGCC

P   V   L       D   S   D   G       S   F   F       L   Y   S       K   L   T   V
1251   TCCCGTGCTG   GACTCCGACG   GCTCCTTCTT   CCTCTATAGC   AAGCTCACCG

D   K   S       R   W   Q       Q   G   N   V       F   S   C       S   V   M
1301   TGGACAAGAG   CAGGTGGCAG   CAGGGGAACG   TCTTCTCATG   CTCCGTGATG

H   E   A   L       H   N   H       Y   T   Q       K   S   L   S       L   S   P
1351   CATGAGGCTC   TGCACAACCA   CTACACGCAG   AAGAGCCTCT   CCCTGTCCCC

G   K   *   (SEQ ID NO: 41)
1401   GGGTAAATGA   (SEQ ID NO: 42)
```

---

The invention claimed is:

1. An isolated nucleic acid encoding an isolated anti-IL13 antibody, or antigen-binding fragment thereof, comprising a light chain comprising the amino acid sequence of SEQ ID NO:39, and a heavy chain comprising the amino acid sequence of SEQ ID NO:41.

2. The nucleic acid of claim 1 comprising the nucleic acid sequence of SEQ ID NO:40 and SEQ ID NO:42.

3. A vector comprising the nucleic acid of claim 1.

4. An isolated host cell comprising the vector of claim 3.

5. An isolated host cell comprising the nucleic acid of claim 1.

6. An isolated nucleic acid encoding an anti-IL-13 antibody, or antigen-binding fragment thereof, comprising H-CDR1, H-CDR2 and H-CDR3 selected from (i)-(ii): (i) SEQ ID NO: 6, SEQ ID NO:8, and SEQ ID NO: 9, respectively; and (ii) SEQ ID NO: 7, SEQ ID NO:8, and SEQ ID NO: 10, respectively; and comprising L-CDR1, L-CDR2 and L-CDR3 selected from (iii)-(v): (iii) SEQ ID NO: 16, SEQ ID NO: 19, and SEQ ID NO: 20, respectively; (iv) SEQ ID NO: 17, SEQ ID NO: 19, and SEQ ID NO: 21, respectively; and (v) SEQ ID NO: 18, SEQ ID NO: 19, and SEQ ID NO: 22, respectively.

7. The nucleic acid according to claim 6, wherein the antibody comprises a heavy chain variable region having an amino acid sequence selected from any one of SEQ ID NO: 23, 27, 31 and 35.

8. The nucleic acid according to claim 7, wherein the nucleic acid comprises the nucleic acid sequence selected from any one of SEQ ID NOs: 24, 28, 32 and 36.

9. The nucleic acid according to claim 6, which comprises a light chain variable region comprising the amino acid sequence selected from any one of SEQ ID NO: 25, 29, 33 and 37.

10. The nucleic acid according to claim 9, which comprises the nucleic acid sequence selected from any one of SEQ ID NOs: 26, 30, 34 and 38.

11. The nucleic acid of claim 6, wherein the antibody, or antigen-binding fragment thereof, comprises a heavy chain variable region comprising an amino acid sequence selected from any one of SEQ ID NO: 23, 27, 31 and 35, and a light chain variable region comprising the amino acid sequence selected from any one of SEQ ID NO: 25, 29, 33 and 37.

12. The nucleic acid of claim 11, which comprises a heavy chain variable region encoded by the nucleic acid sequence selected from any one of SEQ ID NOs: 24, 28, 32 and 35, and a light chain variable region encoded by the nucleic acid sequence selected from any one of SEQ ID NOs: 26, 30, 34 and 38.

13. The nucleic acid according to claim 11, wherein the antibody comprises a heavy chain variable region comprising the amino acid sequence of SEQ ID NO:23 and a light chain variable region comprising the amino acid sequence of SEQ ID NO:25.

14. The nucleic acid according to claim 13, wherein the heavy chain variable region is encoded by a nucleic acid sequence of SEQ ID NO:24 and the light chain variable region is encoded by a nucleic acid sequence of SEQ ID NO:26.

15. The nucleic acid according to claim 11, wherein the antibody comprises a heavy chain variable region comprising the amino acid sequence of SEQ ID NO: 27 and a light chain variable region comprising the amino acid sequence of SEQ ID NO: 29.

16. The nucleic acid according to claim 15, wherein the heavy chain variable region is encoded by a nucleic acid sequence of SEQ ID NO:28 and the light chain variable region is encoded by a nucleic acid sequence of SEQ ID NO:30.

17. The nucleic acid according to claim 11, wherein the antibody comprises a heavy chain variable region comprising the amino acid sequence of SEQ ID NO: 31 and a light chain variable region comprising the amino acid sequence of SEQ ID NO: 33.

18. The nucleic acid according to claim 17, wherein the heavy chain variable region is encoded by a nucleic acid sequence of SEQ ID NO:32 and the light chain variable region is encoded by a nucleic acid sequence of SEQ ID NO:34.

19. The nucleic acid according to claim 11, wherein the antibody comprises a heavy chain variable region comprising the amino acid sequence of SEQ ID NO: 35 and a light chain variable region comprising the amino acid sequence of SEQ ID NO: 37.

20. The nucleic acid according to claim 19, wherein the heavy chain variable region is encoded by a nucleic acid sequence of SEQ ID NO:36 and the light chain variable region is encoded by a nucleic acid sequence of SEQ ID NO:38.

* * * * *